(12) United States Patent
Dutta

(10) Patent No.: US 11,285,147 B2
(45) Date of Patent: Mar. 29, 2022

(54) NEUROPROTECTIVE AGENTS FOR TREATMENT OF NEURODEGENERATIVE DISEASES

(71) Applicant: WAYNE STATE UNIVERSITY, Detroit, MI (US)

(72) Inventor: Aloke K. Dutta, Troy, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 16/562,942

(22) Filed: Sep. 6, 2019

(65) Prior Publication Data
US 2020/0078356 A1 Mar. 12, 2020

Related U.S. Application Data

(63) Continuation-in-part of application No. 16/124,974, filed on Sep. 7, 2018, now Pat. No. 10,874,669.

(51) Int. Cl.
| | |
|---|---|
| A61K 31/495 | (2006.01) |
| A61K 31/135 | (2006.01) |
| A61K 31/427 | (2006.01) |

(52) U.S. Cl.
CPC .......... *A61K 31/495* (2013.01); *A61K 31/135* (2013.01); *A61K 31/427* (2013.01)

(58) Field of Classification Search
CPC ................ A61K 31/495; A61K 31/135; A61K 31/427
See application file for complete search history.

(56) References Cited

U.S. PATENT DOCUMENTS

| | | | |
|---|---|---|---|
| 6,982,332 | B2 | 1/2006 | Dutta |
| 10,125,127 | B2 | 11/2018 | Dutta |
| 2005/0032586 | A1 | 10/2005 | Bennet |
| 2006/0020132 | A1 | 1/2006 | Dutta |
| 2011/0046153 | A1 | 2/2011 | Holger et al. |
| 2012/0108815 | A1 | 5/2012 | Wayne |
| 2015/0299180 | A1 | 10/2015 | Dutta |

FOREIGN PATENT DOCUMENTS

| | | |
|---|---|---|
| WO | 96/08228 A2 | 3/1996 |
| WO | 02/098367 A2 | 12/2002 |
| WO | 2010/123995 A2 | 10/2010 |
| WO | 2014/085600 A1 | 6/2014 |

OTHER PUBLICATIONS

Chemical Abstracts Service CAS Registry Nos. 1380042-93-4, 1380014-61-8, 636607-56-2, and 858357-51-4, CAplus database entry dates of Jun. 25, 2012, Jun. 25, 2012, Jan. 12, 2004 and Aug. 4, 2005, respectively.*
Chemical Abstracts Service CAS Registry No. 2109231-43-6, CAplus database entry date of Aug. 7, 2017; 1 .p.*
Modi, G., Journal of medicinal chemistry 57.4 (2014): 1557-1572.*
Dholkawala, F. et al., "Synthesis and characterization of brain penetrant prodrug of neuroprotective D-264: Potential Therapeutic application in the treatment of Parkinson's diseases," European J. of Pharmaceutics and Biopharmaceutics, 2016, v. 103, pp. 62-70.
Non-Final Office Action dated Mar. 17, 2020 for U.S. Appl. No. 16/124,974, filed Sep. 7, 2018, 15 pgs.
Biswas, S., "Further structure—activity relationships study of hybrid 7-{[2-(4-phenylpiperazin-1-yl) ethyl] propylamino)-5, 6, 7, 8-tetrahydronaphthalen-2-ol analogues: identification of a high-affinity D3-preferring agonist with potent in vivo activity with long duration of action." Journal of medicinal chemistry 51.1 (2007): 101-117.
Biswas, S. et al., "Bioisosteric Heterocyclic Versions of 7-{[2-(4-Phenyl-piperazin-1-yl)ethyl]propy Identification of Highly Potent and Selective Agonists for Dopamine D3 Receptor with Potent In Vivo Activity." J. Med. Che. 2008, 51, pp. 3005-3019.
Brown, D.A., "Investigation of various N-heterocyclic substituted piperazine versions of 5/7-{[2-(4-aryl-piperazin-1-y1)-ethy1]-propyl-amino)-5, 6, 7, 8-tetrahydro-naphthalen-2-ol: Effect on affinity and selectivity for dopamine D3 receptor." Bioorganic & medicinal chemistry 17.11 (2009): 3923-3933.
Brown, D.A., "Structurally constrained hybrid derivatives containing octahydrobenzo [g or f] quinoline moieties for dopamine D2 and D3 receptors: binding characterization at D2/D3 receptors and elucidation of a pharmacophore model." Journal of medicinal chemistry 51.24 (2008): 7806.
Chen, J., "High-affinity and selective dopamine D 3 receptor full agonists." Bioorganic & medicinal chemistry letters 22.17 (2012): 5612-5617.
Dutta, A.K., "A novel series of hybrid compounds derived by combining 2-aminotetralin and piperazine fragments: Binding activity at D 2 and D 3 receptors," Bioorganic & Medicinal Chemistry Ltrs 12.4 (2002): 619-622.
Dutta, A.K., "Synthesis and biological characterization of novel hybrid 7-{[2-(4-phenyl-piperazin-1-yl)-ethyl]-propyl-amino)-5, 6, 7, 8-tetrahydro-naphthalen-2-ol and their heterocyclic bioisosteric analogues for dopamine D2 and D3 receptors," Bioorganic & Medicinal Chemistry, 12, 16 (2004), pp. 4361-4373.
Ghosh, B., "Development of (S)-N6-(2-(4-(Isoquinolin-1-yl) piperazine-1-yl) ethyl)-N6-propyl-4, 5, 6, 7-tetrahydrobenzo [d]-thiazole-2, 6-diamine and its analogue as a D3 receptor preferring agonist: Potent in vivo activity in Parkinson's disease animal models," J. of Medicinal Chemistry 53.3 (2010, p. 1023.
Ghosh, B., "Development of (S)-N6-(2-(4-(Isoquinolin-1-yl) piperazine-1-yl) ethyl)-N6-propyl-4, 5, 6, 7-tetrahydrobenzo [d]-thiazole-2, 6-diamine and its analogue as a D3 receptor preferring agonist: Potent in vivo activity in Parkinson's disease animal models," J. of Medicinal Chemistry 53.3 (2010, p. 1023.

(Continued)

*Primary Examiner* — John M Mauro
(74) *Attorney, Agent, or Firm* — Brooks Kushman P.C.

(57) ABSTRACT

A compound having formula I is useful for treating a neurodegenerative disease:

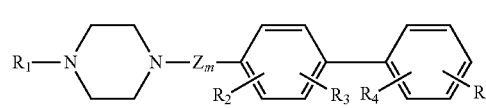

I or a pharmaceutically acceptable salt or ester thereof, wherein $R_1$, $R_2$, $R_3$, $R_4$, $R_5$, $R_6$, $R_7$, $R_8$ are each indepen- (Continued)

dently hydroxyl, $C_{1-4}$ alkyl, $C_{1-4}$ alkoxyl, $C_{1-8}$ alkyl, $C_{2-8}$ alkenyl, $C_{2-8}$ alkynyl, $C_{4-8}$, are specified substituents.

25 Claims, 6 Drawing Sheets

(56) References Cited

OTHER PUBLICATIONS

Ghosh, B., "Further delineation of hydrophobic binding sites in dopamine D 2/D 3 receptors for N-4 substituents on the piperazine ring of the hybrid template 5/7-{[2-(4-aryl-piperazin-1-y1)-ethyl]propyl-amino)-5, 6, 7, 8-tetrahydro-naphthalen-2-ol." Bioorganic & medicinal chemistry 18.15 (2010): 5661-5674. Ghosh, B., "Discovery of 4-(4-(2-((5-hydroxy-1, 2, 3, 4-tetrahydronaphthalen-2-yl)(propyl) amino)-ethyl) piperazin-1-yl) quinolin-8-ol and its analogues as highly potent dopamine D2/D3 agonists and as iron chelator: In vivo activity indicates potential application in symptomatic and neuroprotective therapy for Parkinson's Disease," J. Med. Chem. 2010, 53, pp. 2114-2125.

Johnson, M. et al., Correctior to Structure-Activity Relationship Study of N6-(2-(4-(1H-Indol-5-yl)piperazin-1-yl) ethyl)-N6-propyl-4, 5, 6, 7-tetrahydrobenzol[d]thiazole-2, 6-diamine Analogues: Development of Highly Selective D3 Dopamine Receptor Agonists along with a Highly Potent D2/D3 Agonist and Their Pharmacological Characterization, J. of J. Med. Chem., Jan. 4, 2013, 56, pp. 589-590.

Johnson, M. et al., "Structure-Activity Relationship Study of N6-(2(4-(1H-indol-5-yl)piperazin-1-yl)ethyl)-N6-propy-4, 5, 6, 7-tetrahydrobenzo[d]thiazole-2,6-diamine analogues: Development of highly selective D3 dopamine receptor agonists along with a highly potent D2/D3 agonist and their pharmacological characterization," J Med Chem. 2012, 55(12), pp. 5826-5840.

Kortagere, S., "Interaction of novel hybrid compounds with the D3 dopamine receptor: Site-directed mutagenesis and homology modeling studies." Biochemical pharmacology 81.1 (2011): 157-163.

Wang, C.H. et al., "Novel synthesis and functionalization of orth-ortho disubstituted biphenyls and a highly condensed novel heterocycle using radical cylization reaction," Tetrahedron 68 (2012, pp. 9750-9762.

International Search Report dated Mar. 5, 2014 from PCT/US2013/072253, filed Nov. 27, 2013, 3 pgs.

Partial Supplementary European Search Report dated Jun. 13, 2016 for EP Appn. No. 13859526.9, 2 pgs.

Non-final Office Action dated Jul. 31, 2019 for U.S. Appl. No. 16/154,301, filed Oct. 8, 2018, 18 pgs.

Non-final Office Action dtd Aug. 12, 2019 for U.S. Appl. No. 16/124,974, filed Sep. 7, 2018, 23 pgs.

Int'l Search Report dated Jan. 2, 2020 for PCT/US2019/049927 filed Sep. 6, 2019, 11 pgs.

Caplus-Registry Nos. 1027589-19-0, 1027223-61-5, and 80119-88-6, having database entry dates of Jun. 12, 2008, Jun. 11, 2008, and Nov. 16, 1984, respectively (entries accessed Jul. 17, 2019), p. 1.

Modi, G. et al., "Multifunctional D2/D3 agonist D-520 with high in vivo efficacy: modulator of toxicity of alpha-synuclein aggregates," ACS Chemical Neuroscience, 2014, v. 5, n. 8, pp. 700-717.

Modi, G. et al., "Understanding the structural requirements of hybrid (S)-6-((2-(4-phenylpiperazin-1-y1) ethyl) (propyl) amino)-5, 6, 7, 8 -tetrahydronaphthalen-1-ol and its analogs as D2/D3 receptor ligands: a 3D QSAR investigation," Med. Chem. Comm., 2014, v. 5, n. 9, pp. 1384-1399.

Yedlapudi, D. et al., Inhibition of alpha-synuclein aggregation by multifunctional dopamine agonists assessed by a novel in vitro assay and an in vivo *Drosophila* synucleinopahty model, Scientific Reports, 2016, v. 6, n. 38510, pp. 1-12.

\* cited by examiner

Scheme 3

Reagents and conditions: a) Dess-Martin periodinane, CH$_2$Cl$_2$, rt, 4 h; b) NaBH(OAc)$_3$, CH$_2$Cl$_2$, rt, 48 h; c) 48% aq. HBr, reflux, 5 h.

Scheme 4

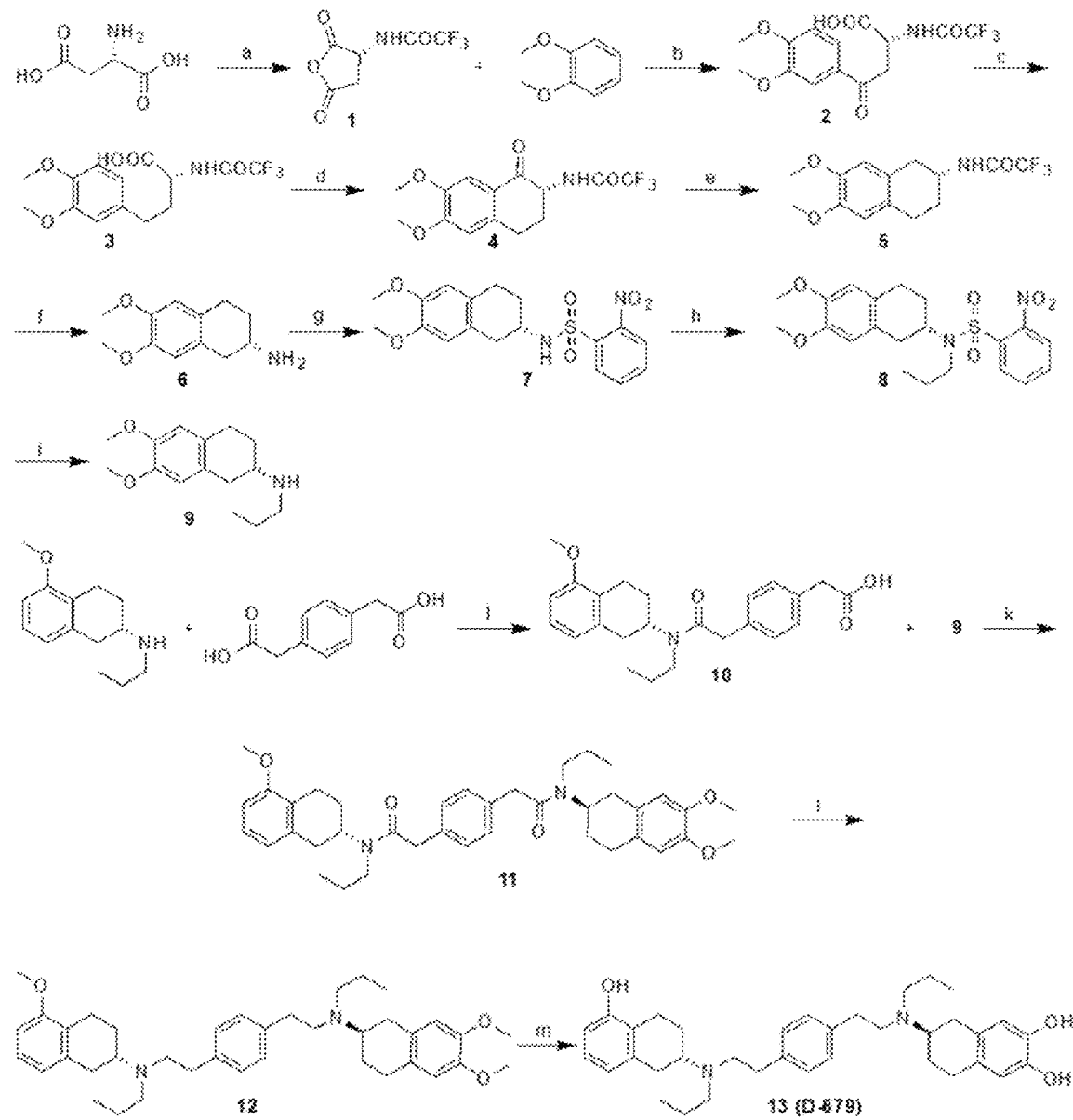

Reagents and conditions: a) Trifluoroacetic anhydride, CF₃COOH, -60 °C to rt to reflux, 2 h; b) AlCl₃, CH₂Cl₂, rt, 4 days; c) Et₃SiH, CF₃COOH, reflux, 2 h; d) i) PCl₅, CH₂Cl₂, 0 °C, 1 h; ii) SnCl₄, 0 °C to rt, 4 h; e) Et₃SiH, BF₃·Et₂O, rt, 48 h; f) K₂CO₃, MeOH/H₂O, reflux, 4 h; g) 2-Nitrobenzenesulfonyl chloride, Et₃N, THF, -10 °C to rt, 1.5 h; h) 1-Bromopropane, K₂CO₃, CH₃CN, 40 °C, 48 h; i) Thioglycolic acid, K₂CO₃, DMF, 0 °C to rt to 50 °C, 16 h; j) EDC, HOBt, Et₃N, DMF, rt, 4 h; k) EDC, HOBt, Et₃N, DMF, rt, overnight; l) BH₃·THF, THF, rt to 55 °C, 4 h; m) 48% aq. HBr, reflux, 5 h.

Fig. 6

NEUROPROTECTIVE AGENTS FOR TREATMENT OF NEURODEGENERATIVE DISEASES

CROSS-REFERENCE TO RELATED APPLICATIONS

This application is a continuation-in-part of U.S. Ser. No. 16/124,974 filed Sep. 7, 2018, now U.S. Pat. No. 10,874,669 issued Dec. 29, 2020.

STATEMENT REGARDING FEDERALLY SPONSORED RESEARCH OR DEVELOPMENT

The invention was made with Government support under Contract No. NS047198 awarded by the National Institutes of Health/National Institute of Neurological Disorders and Stroke. The Government has certain rights to the invention.

TECHNICAL FIELD

The present invention relates to compounds for treating neurodegenerative diseases.

BACKGROUND OF THE INVENTION

Dopaminergic receptor systems have been targeted for the development of pharmacotherapeutic agents for a number of CNS related disorders, including drug addiction, schizophrenia, depression, and Parkinson's disease (PD). Dopamine (DA) receptor agonists have been employed more extensively in the treatment of Parkinson's disease than any other type of pharmacotherapy. Levodopa (L-dopa), the immediate precursor to endogenous DA, is the current gold-standard treatment option for PD. DA receptors belong to the family of transmembrane proteins known as G-protein-coupled receptors (GPCRs). DA receptors are widely distributed in the CNS, are also present in the periphery, and are divided into five subtypes. On the basis of the stimulatory action on adenylyl cyclase, D1 and D5 are grouped together as D1 type. D2-D4 receptors are classified as D2 type because of their inhibitory action on adenylyl cyclase activity. Interestingly, the D3 receptor was found to have a distribution in the brain that is somewhat different from that of the D2 receptor. The highest levels of D3 receptor expression were found to be in the limbic region of the brain, while D2 receptor expression is most dense in the striatum of the midbrain. D2 and D3 receptor subtypes occur post- and presynaptically. In the latter location they function as autoreceptors that regulate DA synthesis, metabolism, and release. It is noteworthy that D2 and D3 receptor subtypes share 50% overall amino acid sequence homology and 75-80% in their agonist binding sites. As a result, development of ligands selective for either subtype is a challenging task.

Parkinson's disease (PD) is a progressive, neurodegenerative disorder that results from the death of DA-producing cells in the substantia nigra region of the midbrain. Common symptoms include resting tremor, muscular rigidity, bradykinesia, postural instability, and cognitive psychiatric complications. Although the etiology of PD is not yet clear and may be multifactorial, oxidative stress and mitochondrial dysfunction are thought to play a central role in the pathology of the disease. Recent studies on various genetic mutations have provided new insights into the disease process. Oxidative stress has been strongly implicated in midbrain dopaminergic cell death. Toxicity from endogenous and exogenous origins, caused by oxidative mechanisms, has been implicated as a fundamental process in progressive nigral cell loss. Along with motor fluctuations and wearing off after long-term treatment, side effects associated with L-dopa treatment and the eventual oxidation of DA derived from L-dopa have been speculated to produce further oxidative stress.

In addition, α-synuclein, a presynaptic protein involved in fibrillization, has been implicated in the pathogenesis of PD. A recent report demonstrated that in cultured human dopaminergic neurons, accumulation of α-synuclein induces apoptosis in the presence of DA and reactive oxygen species. Furthermore, an interaction between calcium, cytosolic DA, and α-synuclein has been implicated in the loss of DA neurons in the substantia nigra. In this case, DA dependent neurotoxicity is mediated by a soluble protein complex containing α-synuclein. Therefore, α-synuclein, together with oxidized DA, could have synergistic effects in terms of disease susceptibility and progression.

Accordingly, there is a need for dopamine improved D2/D3 agonist molecules, and in particular, for improved D2/D3 agonist molecules with a capacity to bind to iron.

SUMMARY OF THE INVENTION

In at least one embodiment, the present invention solves one or more problems of the prior art by providing a compound having formula I for treating a neurodegenerative disease:

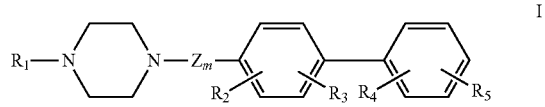

wherein:

$R_1$ is H, $C_{1-8}$ alkyl, $C_{2-8}$ alkenyl, $C_{4-8}$ cycloalkyl, $C_{4-8}$ cycloalkenyl, $C_{6-10}$ aryl, $C_{1-10}$ alkyl $C_{6-10}$ aryl, or

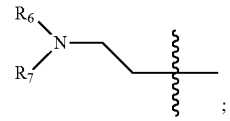

$R_2$, $R_3$, $R_4$, $R_5$ are each independently H or OH wherein at least 2 of $R_2$, $R_3$, $R_4$, $R_5$ are OH;

$R_6$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{6-10}$ aryl,

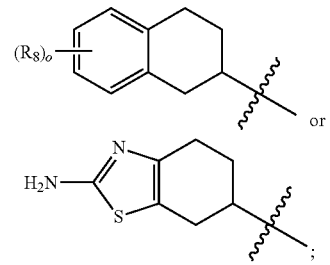

$R_7$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-9}$ cycloalkenyl, or $C_{6-10}$ aryl;

$R_8$ are each independently hydroxyl, $C_{1-4}$ alkyl, $C_{1-4}$ alkoxyl, $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, $-NR^3{}_q$ or $C_{1-10}$ hydrocarbon groups optionally containing one or more O, N, S, or Se heteroatoms where $R^3$ individually are H or organyl groups (e.g., $C_{1-8}$ alkyl, $C_{2-8}$ alkenyl, $C_{2-8}$ alkynyl, $C_{4-8}$ cycloalkyl, $C_{4-8}$ cycloalkenyl, or $C_{6-10}$ aryl) and q is 2 or 3, with the proviso that when q is 3, the group bears a positive formal charge (with an appropriate counter ion (e.g., halide) being present);

$Z_m$ is absent or a divalent linking moiety in which Z is repeated m times;

o is 0, 1, 2, 3, or 4; and m is 0, 1, 2, 3, 4, or 5.

In another embodiment, a compound having formula II for treating a neurodegenerative disease is provided:

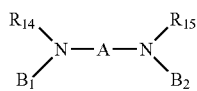

II or a pharmaceutically acceptable salt or ester thereof, wherein:

A is an optionally substituted $C_{6-12}$ aryl or $C_{6-12}$ heteroaryl;

$R_{14}$, $R_{15}$ are each independently H, $C_{1-8}$ alkyl, $C_{1-8}$ alkyl, $C_{2-4}$ alkenyl, $C_{4-8}$ cycloalkyl, $C_{4-8}$ cycloalkenyl, $C_{6-10}$ aryl, or $C_{1-10}$ alkyl, or $C_{6-10}$ aryl;

$B_1$ and $B_2$ are each independently:

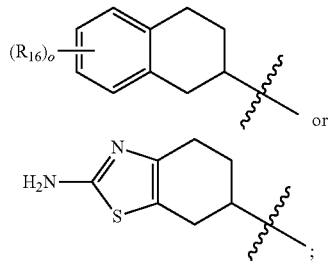

and o is 0, 1, 2, 3, or 4; and $R_{16}$ is an optional substituent.

BRIEF DESCRIPTION OF THE DRAWINGS

Exemplary embodiments of the present invention will become more fully understood from the detailed description and the accompanying drawings, wherein:

FIG. 6. Synthetic Scheme 4 for compounds that are useful for treating a neurodegenerative disease.

DETAILED DESCRIPTION OF THE INVENTION

Figure 1:
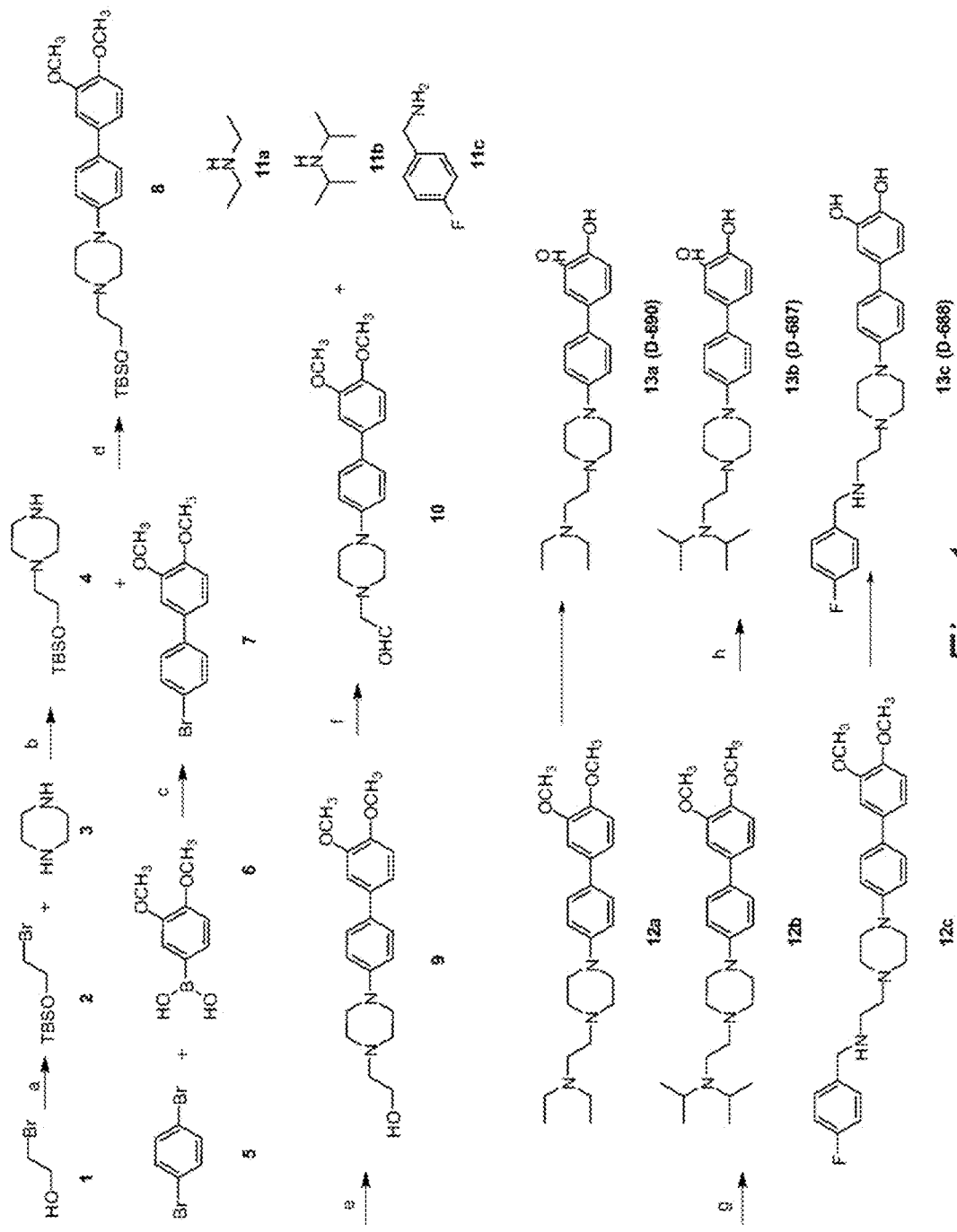
FIG. 1. Synthetic Scheme 1 for compounds that are useful for treating a neurodegenerative disease.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include hydrogen, alkyl, lower alkyl, $C_{1-6}$ alkyl, $C_{6-10}$ aryl, $C_{6-10}$ heteroaryl, $-NO_2$, $-NH_2$, $-N(R'R'')$, $-N(R'R''R''')^+L^-$, Cl, F, Br, $-CF_3$, $-CCl_3$, $-CN$, $-SO_3H$, $-PO_3H_2$, $-COOH$, $-CO_2R'$, $-COR'$, $-CHO$, $-OH$, $-OR'$, $-O^-M^+$, $-SO_3^-M^+$, $-PO_3^-M^+$, $-COO^-M^+$, $-CF_2H$, $-CF_2R'$, $-CFH_2$, and $-CFR'R''$ where R', R'' and R''' are $C_{1-10}$ alkyl or $C_{6-18}$ aryl groups (it should be appreciated that these groups can be in addition to other groups listed for a specific R group); single letters (e.g., "n" or "o") are 1, 2, 3, 4, or 5; in the compounds disclosed herein a CH bond can be substituted with alkyl, lower alkyl, $C_{1-6}$ alkyl, $C_{6-10}$ aryl, $C_{6-10}$ heteroaryl, $-NO_2$, $-NH_2$, $-N(R'R'')$, $-N(R'R''R''')^+L^-$, Cl, F, Br, $-CF_3$, $-CCl_3$, $-CN$, $-SO_3H$, $-PO_3H_2$, $-COOH$, $-CO_2R'$, $-COR'$, $-CHO$, $-OH$, $-OR'$, $-O^-M^+$, $-SO_3^-M^+$, $-PO_3^-M^+$, $-COO^-M^+$, $-CF_2H$, $-CF_2R'$, $-CFH_2$, and $-CFR'R''$ where R', R'' and R''' are $C_{1-10}$ alkyl or $C_{6-18}$ aryl groups; percent, "parts of," and ratio values are by weight; the term "polymer" includes "oligomer," "copolymer," "terpolymer," and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4, . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g. pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

Throughout this application, where publications are referenced, the disclosures of these publications in their entireties are hereby incorporated by reference into this application to more fully describe the state of the art to which this invention pertains.

In a variation, the term "organyl group" means any organic substituent group, regardless of functional type, having one free valence at a carbon atom. Examples of organyl group include but are not limited to $C_{1-8}$ alkyl, $C_{2-8}$ alkenyl, $C_{2-8}$ alkynyl, $C_{4-8}$ cycloalkyl, $C_{4-8}$ cycloalkenyl, $C_{6-10}$ aryl, $C_{2-10}$ alkanediyl, $C_{1-8}$ alkoxy, $C_{1-8}$ thioalkoxy, $C_{5-18}$ cycloalkyl, and the like. More specific examples includes, but are not limited to methyl, ethyl, propyl, butyl, pyridinyl, 4-pyridylmethyl, and the like.

In a variation, the term "alkyl" means a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

In a variation, the term "alkanediyl" means a straight or branched hydrocarbon diradical having from 1 to 10 carbon atoms formed by removing 2 hydrogen atoms from an alkane.

In a variation, the term "alkoxy" and "thioalkoxy" are O-alkyl or S-alkyl of from 1 to 8 carbon atoms as defined above for "alkyl".

In a variation, the term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

In a variation, the term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

In a variation, the term "alkenediyl" means a straight or branched hydrocarbon diradical having from 2 to 12 carbon atoms formed by removing 2 hydrogen atoms from a $C_{2-12}$ alkene.

In a variation, the term "alkynyl" means a straight or branched triple bonded unsaturated hydrocarbon radical having from 2 to 12 carbon atoms and includes, for example, ethynyl, 2-propynyl, 3-butynyl, 4-pentynyl, 5-hexynyl, 6-heptynyl, 7-octynyl, 8-nonynyl, 9-decynyl, 10-undecynyl, 11-dodecynyl, and the like.

In a variation, the term "alkynediyl" means a straight or branched hydrocarbon diradical having from 2 to 12 carbon atoms formed by removing 2 hydrogen atoms from a $C_{2-12}$ alkyne.

In a variation, the term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

In a variation, the term "heterocycloalkyl" means a saturated hydrocarbon ring having 3 to 8 carbon atoms in which 1 or more carbon atoms are replaced by N, S, O, Se, etc. Examples includes 2- or 3-tetrahydrothieno, 2- or 3-tetrahydrofuran, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl.

In a variation, the term "aryl" means an aromatic radical such as a phenyl group, a naphthyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano-$SO_2NH_2$, or nitro, or a naphthyl group substituted by 1 to 4 substituents as defined above for a phenyl group substituted by 1 to 4 substituents. In a refinement, aryl is a $C_{6-14}$ aryl.

In a variation, the term "heteroaryl" means a $C_{5-13}$ heteroaromatic radical such as 2- or 3-thienyl; 2- or 3-furanyl; 1-, 2- or 3-pyrrolyl; 1-, 2-, 4-, or 5-imidazolyl; 1-, 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 1-, 3-, or 5-1,2,4-triazolyl; 1-, 2-, 4-, or 5-1,2,3-triazolyl; 1- or 5-tetrazolyl; 4-, or 5-1,2,3-oxadiazolyl; 3-, or 5-1,2,4-oxadiazolyl; 2-1,3,4-oxadiazolyl; 2-1,3,4-thiadiazoyl; 2-1,3,5-triazinyl; 3-pyridinyl; 3-, 4-, or 5-pyridazinyl; 2-pyrazinyl; 2-, 4-, or 5-pyrimidinyl; unsubstituted or substituted by 1 to 2 substituents selected from $NH_2$, OH, S, halogen as defined hereinafter, alkyl as defined above, or alkoxy as defined above. In a refinement, heteroaryl is a $C_{5-10}$ heteroaryl.

In a variation, the term "halogen" or "halo" means fluorine, chlorine, bromine, or iodine.

Abbreviations

"BINAP" means 2,2'-bis(diphenylphosphino)-1,1'-binaphthyl
"DMSO" is dimethylsulfoxide;
"DA" means dopamine.
"et" is ethyl;
"me" is methyl;
"h" is hour;
"L-DOPA" means (S)-(3,4-dihydroxyphenyl) alanine.
"$NaBH(OAc)_3$" means sodium triacetoxyborohydride.
"PD: Parkinson's disease.
"$Pd(OAc)2$" means palladium(II) acetate.
"s" is seconds;
"$SO_3.py$" means sulfur trioxide pyridine.
"rt" is room temperature;
"TBAF" is tetra-n-butylammonium fluoride;
"THF" is tetrahydrofuran;
"TBS" means tert-butyldimethylsilyl.

In at least one embodiment, the present invention provides a compound having formula I for treating a neurodegenerative disease:

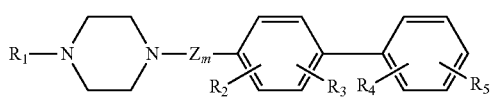

I or a pharmaceutically acceptable salt or ester thereof, wherein:

$R_1$ is H, $C_{1-8}$ alkyl, $C_{2-8}$ alkenyl, $C_{4-8}$ cycloalkyl, $C_{4-8}$ cycloalkenyl, $C_{6-10}$ aryl, $C_{1-10}$ alkyl $C_{6-10}$ aryl, or

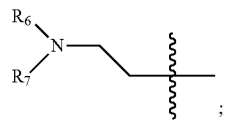

$R_2$, $R_3$, $R_4$, $R_5$ are each independently H or OH wherein in a refinement at least 2 of $R_2$, $R_3$, $R_4$, $R_5$ are OH. In another refinement, 3 of $R_2$, $R_3$, $R_4$, $R_5$ are OH. In still another refinement, each of (i.e., all of) $R_2$, $R_3$, $R_4$, $R_5$ are OH;

$R_6$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, an optionally substituted $C_{6-10}$ aryl,

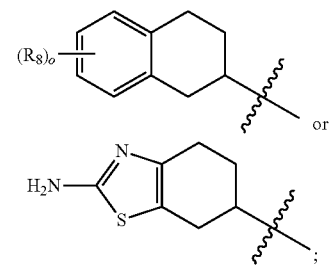

$R_7$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, or an optionally substituted $C_{6-10}$ aryl;

$R_8$ are each independently hydroxyl, $C_{1-4}$ alkyl, $C_{1-4}$ alkoxyl, $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, —$NR^3_q$ or $C_{1-10}$ hydrocarbon groups optionally containing one or more O, N, S, or Se heteroatoms where $R^3$ individually are H or organyl groups and q is 2 or 3, with the proviso that when q is 3, the group bears a positive formal charge; and $Z_m$ is absent or a divalent linking moiety in which Z is repeated m times;

o is 0, 1, 2, 3, or 4 (when o is 0 all substituents are hydrogen (H)); and m is an integer from 0 to 5. In a refinement, the compound of claim 1 wherein $R_6$ and $R_7$ are each independently $C_{1-8}$ alkyl, $C_{2-8}$ alkenyl, $C_{2-8}$ alkynyl, $C_{4-8}$ cycloalkyl, or $C_{4-8}$ cycloalkenyl.

In a refinement, $R_7$ is substituted with a component selected from the group consisting of halogen, $C_{1-8}$ alkyl, $C_{1-8}$ alkoxy, $C_{1-4}$ acyloxy, $C_{1-4}$ acyl, —C(O)—$R_9$, —$R_{10}$—NH—$SO_2$—N($R_9$)r, —$R_{10}$—NH—C(O)—$R_9$; —$R_{10}$—N($R_9$)$_r$, and —$R_{10}$—Ar where:

$R_9$ is H, $C_{1-8}$ alkyl, $C_{2-8}$ alkenyl, $C_{4-8}$ cycloalkyl, $C_{4-8}$ cycloalkenyl, or $C_{6-10}$ aryl;
$R_{10}$ is $C_{2-8}$ alkenyl;
r is 2 or 3; and
Ar is a $C_{6-10}$ aryl ring system, optionally including one or more heteroatoms or $C_{5-10}$ heteroaryl; with the proviso that when r is 3, the nitrogen of the N($R_9$)$_r$ group will bear a positive formal charge. In a further refinement, Ar is an optionally substituted phenyl, thienyl, pyridyl, bipyridyl, biphenylyl, or naphthyl.

In another refinement, $R_8$ are hydroxyl, $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl; $C_{6-10}$ aryl, $-N(R_{11})_q-NH-C(O)-R_{11}$, or $-NH-C(O)-N(R_{12})_2$, where $R_{11}$ individually are H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl where q is 2 or 3, with the proviso that when q is 3, the group bears a positive formal charge and wherein the hydrocarbon groups in each case are optionally substituted with $-CN$, $C_{1-8}$ alkyl, $-OR_{13}$, $-OH$, halo, or $-CF_3$ where $R_{13}$ is $C_{1-8}$ alkyl.

When present, Z can be $-CH_2-$, $-CHOHCH_2-$, $-CHOHCH_2CH_2-$, $-CHOHCH_2CH_2CH_2-$, $-CO-$, $-N-CH_2-$, $-N-CO-$, $-(CH_2)_n-$, $-CHOH(CH_2)_n-$, $-(CH_2)_nCO-$, $-(CH_2)_nNCO(CH_2)_k-$, $C_{1-10}$ carboximido, $C_{1-10}$ alkanediyl, $C_{2-10}$ alkanediyl, $C_{2-10}$ alkynediyl, and combinations thereof; m is 1, 2, 3, 4, or 5; and n and k are each independently integers 0, 1, 2, 3, 4, 5, 6, 7, or 8.

In a variation, more specific compounds having formula I are provided by the following formula:

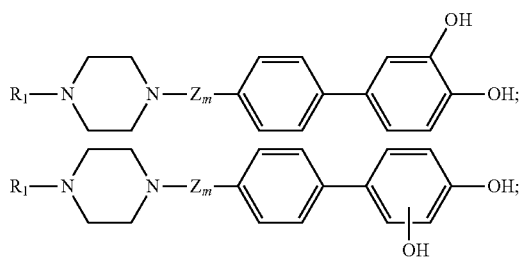

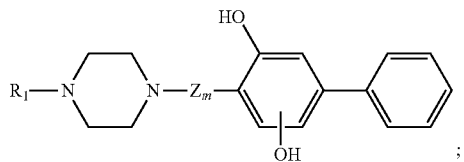

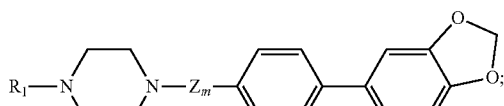

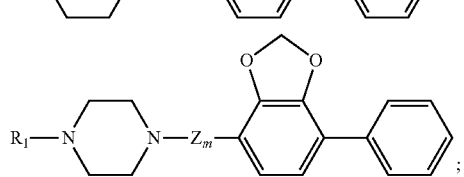

and pharmaceutically acceptable salts and esters thereof.

In another variation, more specific compounds having formula I are provided by the following formula:

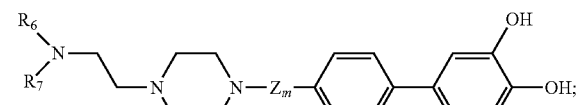

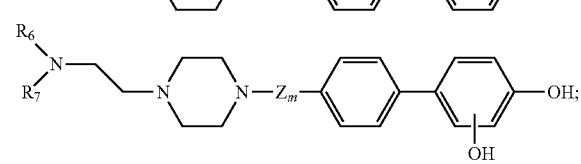

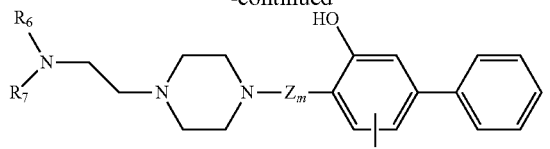

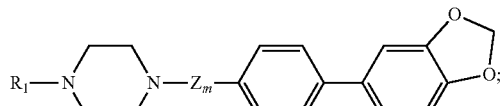

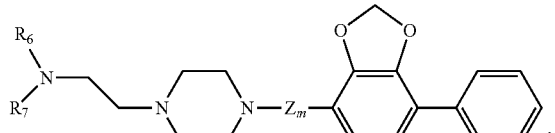

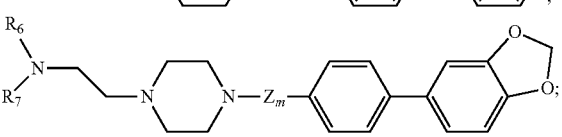

and pharmaceutically acceptable salts and esters thereof.

Specific useful compounds having formula I are the following compounds:

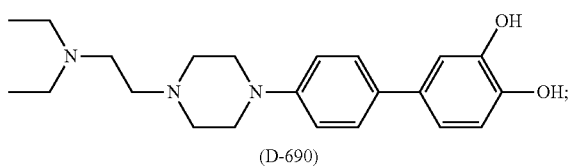

(D-690)

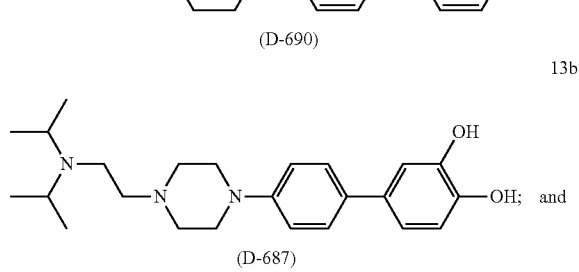

(D-687)

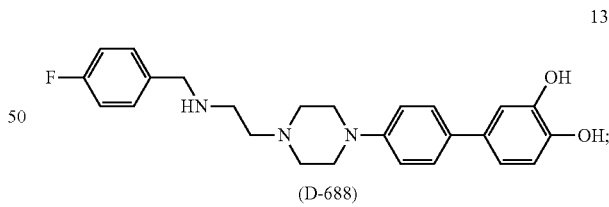

(D-688)

and pharmaceutically acceptable salts and esters thereof.

In another embodiment, a compound having formula II for treating a neurodegenerative disease is provided:

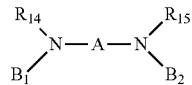

II or a pharmaceutically acceptable salt or ester thereof, wherein:

A is an optionally substituted $C_{6-12}$ aryl or $C_{6-12}$ heteroaryl;

$R_{14}$, $R_{15}$ are each independently H, $C_{1-8}$ alkyl, $C_{2-8}$ alkenyl, $C_{4-8}$ cycloalkyl, $C_{4-8}$ cycloalkenyl, $C_{6-10}$ aryl, $C_{1-10}$ alkyl, or $C_{6-10}$ aryl;

$B_1$ and $B_2$ are each independently

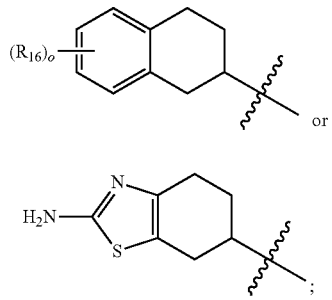

o is 0, 1, 2, 3, or 4; and $R_{16}$ is an optional substituent as set forth above for example of R group substituents.

In a variation of the compounds having formula II, A is optionally substituted phenyl:

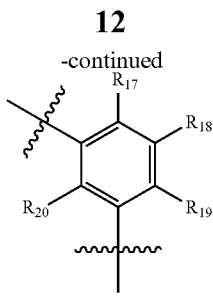

where $R_{17}$, $R_{18}$, $R_{19}$, $R_{20}$ are each independently H, $C_{1-8}$ alkyl, OH, or halide (e.g., F, Cl, Br, I) or any R group substituent set forth above. In a refinement, A is a substituted phenyl having 1, 2, 3, or 4 hydroxyl groups. In a further refinement, A is:

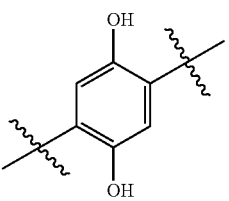

In another variation, more specific compounds having formula II are provided by the following formula:

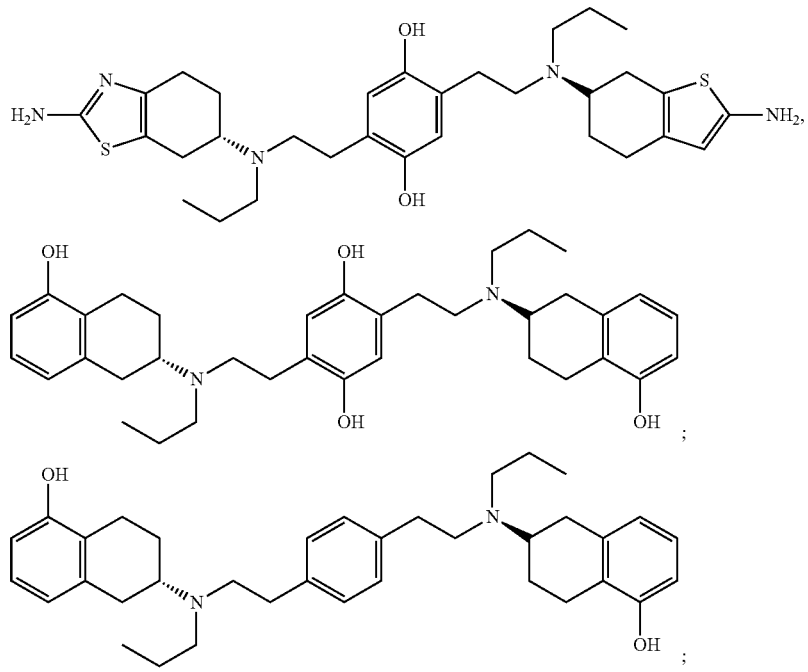

and pharmaceutically acceptable salts and esters thereof.

In another refinement, $R_{16}$ are H, hydroxyl, halogen, nitro, cyano, $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl; $C_{6-10}$ aryl, —N($R_{11})_q$— NH—C(O)—$R_{11}$, or —NH—C(O)—N($R_{12})_2$, where $R_{11}$ individually are H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl where q is 2 or 3, with the proviso that when q is 3, the group bears a positive formal charge and wherein the hydrocarbon groups

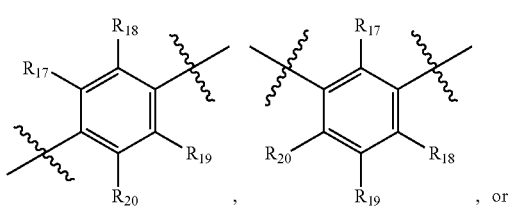

in each case are optionally substituted with —CN, $C_{1-8}$ alkyl, —$OR_{13}$, —OH, halo, or —$CF_3$ where $R_{13}$ is $C_{1-8}$ alkyl.

The compounds set forth herein may be used per se or as pharmaceutically acceptable derivatives. The latter term includes salts, esters, and other derivatives generally considered acceptable by pharmaceutical standards. Useful derivatives, for example, include salts of organic and inorganic acids such as sulfates, phosphates, hydrohalide salts, carboxylate salts, etc., as well as esters of carboxylic acid or hydroxyl substituents, ethers of hydroxyl substituents, amides of amino substituents, as well as carbamates, ureas, etc. Synthesis of these derivatives is conventional, and well known to those skilled in pharmaceutical chemistry. For example, compounds bearing hydroxyl groups may be converted to esters by customary techniques of organic chemistry, such as reaction with an acyl halide, carboxylic acid anhydride, or by esterification with an acid while removing byproduct water. In some cases, derivation may be desired to facilitate compounding of the pharmaceutical into an acceptable form such as tablets, powder, aqueous dispersion, capsule, etc., or may be useful in assisting bioavailability of the drug following administration, for example, by rendering the compound more or less soluble. In many cases, such as, for example, esters, ureas, carbamates, ethers, etc., the derivative may act as "prodrug," which liberates the active form by biological transformation, i.e., by enzymatic hydrolysis of an ester functionality, as is well known to the pharmaceutical chemist.

In another embodiment, a method for treating a subject with a neurodegenerative disease. The method includes a step of identifying a subject having a CNS disease. A therapeutic amount of a compound having formula I or II or any of the variation or refinements thereof is administered to the subject. Examples of such neurodegenerative diseases includes drug addiction, schizophrenia, depression, and Parkinson's disease (PD). Typical dosages for mammalian subjects may vary from 0.001 mg/Kg of body weight to about 100 mg/Kg of body weight, preferably 0.01 mg/Kg to 5 mg/Kg. The actual amount will vary depending upon the particular CNS activity desired to be altered, and the desired degree of alteration. The upper limits may, as with virtually all drugs, be limited by toxicity of the drug or its metabolites, or by the presence of unwanted side effects. The drugs may be administered in any form, but preferably in the form of tablets or capsules with appropriate excipients. Dosages, forms of administration, etc., can be readily determined by those skilled in the art.

Guidelines to the effective dosages in mammalian species are provided by the many known drugs commercially available which bind to CNS monoamine receptor sites, and by comparing the binding affinities of these pharmaceuticals with the target compounds of the subject invention by in vivo and in vitro studies. In addition to the utility of the subject invention compounds in treatment of diseases such as Parkinson's disease, schizophrenia, treatment for addiction such as cocaine addiction, and the like, the subject invention compounds are also useful, particularly in their radio labeled form, for clinical studies directed to distribution of monoamine receptor sites in the brain and the effect which compounds, such as cocaine, have on these sites.

The following examples illustrate the various embodiments of the present invention. Those skilled in the art will recognize many variations that are within the spirit of the present invention and scope of the claims.

FIG. 1 provides a synthetic scheme for compounds having formula 1.

I. Scheme 1 (FIG. 1)

1. (2-Bromo-ethoxy)-tert-butyl-dimethyl-silane

A solution of bromoethanol 1 (1 mL, 14.1 mmol), imidazole (1.9 g, 27.9 mmol), and tert-butyldimethylsilyl chloride (2.1 g, 13.9 mmol) in $CH_2Cl_2$ (15 mL) was stirred at room temperature for 20 h. After the reaction was complete, water (20 mL) was added, and reaction mixture was extracted with $CH_2Cl_2$ (3×50 mL). The $CH_2Cl_2$ layer was dried over $Na_2SO_4$, filtered, and concentrated in vacuo. The resulting crude was purified by column chromatography using 5% ethyl acetate in hexanes to give compound 2 (2.85 g, 86%). $^1$H NMR ($CDCl_3$, 600 MHz): δ ppm 0.09 (s, 6H), 0.91 (s, 9H), 3.40 (t, J=6.6 Hz, 2H), 3.89 (t, J=6.6 Hz, 2H).

2. 1-[2-(tert-Butyl-dimethyl-silanyloxy)-ethyl]-piperazine

A suspension of piperazine 3 (2.3 g, 26.7 mmol), intermediate 2 (2.55 g, 10.7 mmol), and potassium carbonate (11 g, 79.6 mmol) in acetonitrile (35 mL) was refluxed at 80-90° C. for overnight. The reaction mixture was filtered, and the filtrate was condensed in vacuo. The residue was then diluted with ether, washed with water, dried over $Na_2SO_4$, filtered, and concentrated to produce intermediate 4 (2.19 g, 84%). $^1$H NMR ($CDCl_3$, 600 MHz): δ ppm 0.06 (s, 6H), 0.89 (s, 9H), 2.49-2.53 (m, 6H), 2.89 (t, J=4.8 Hz, 4H), 3.76 (t, J=6.6 Hz, 2H).

3. 4'-bromo-3,4-dimethoxy-1,1'-biphenyl

Into a mixture of starting material 5 (5.96 g, 25.3 mmol), $Pd(PPh_3)_4$ (0.73 g, 0.63 mmol), and $K_2CO_3$ (3.5 g, 25.3 mmol) in toluene/$H_2O$ (20 mL/10 mL), a suspension of boronic acid 6 (2.3 g, 12.6 mmol) in ethanol (10 mL) was added and stirred at room temperature for 10 min. The reaction mixture was refluxed at 85-90° C. for 3 h. The solvent was partially evaporated, and the mixture was extracted with ethyl acetate (3×100 mL), which was then concentrated in vacuo after dried over $Na_2SO_4$. The resulting crude was purified by column chromatography using 5-10% ethyl acetate in hexanes to give compound 7 (2.89 g, 78%). $^1$H NMR ($CDCl_3$, 600 MHz): δ ppm 3.93 (s, 3H), 3.95 (s, 3H), 6.94 (d, J=8.4 Hz, 1H), 7.06 (d, J=1.8 Hz, 1H), 7.11 (dd, J=8.4, 2.4 Hz, 1H), 7.42-7.43 (m, 2H), 7.54 (dt, J=8.4, 1.8 Hz, 2H).

4. 1-(2-((tert-butyldimethylsilyl)oxy)ethyl)-4-(3',4'-dimethoxy-[1,1'-biphenyl]-4-yl)piperazine The mixture of intermediate 4 (3.33 g, 13.6 mmol), intermediate 7 (2 g, 6.8 mmol), BINAP (0.425 g, 0.68 mmol), and $Cs_2CO_3$ (6.67 g, 20.5 mmol) in toluene (60 mL) was degassed by bubbling $N_2$ for 5 min. Then $Pd(OAc)_2$ (115 mg, 0.51 mmol) was added quickly followed by degassing for another 5 min. The reaction mixture was refluxed at 110° C. for 24 h under inert condition. Afterward, it was cooled to room temperature, filtered through a pad of celite, washed with $CH_2Cl_2$, and concentrated in vacuo. The resulting crude was purified by column chromatography using 10-30% ethyl acetate in hexanes to give compound 8 (2.4 g, 77%). $^1$H NMR ($CDCl_3$, 600 MHz): δ ppm 0.80 (s, 6H), 0.91 (s, 9H), 2.60 (t, J=6.6 Hz, 2H), 2.71 (t, J=4.8 Hz, 4H), 3.24 (t, J=4.8 Hz, 4H), 3.81 (t, J=5.4 Hz, 2H), 3.91 (s, 3H), 3.94 (s, 3H), 6.91 (d, J=7.8 Hz, 1H), 6.97 (d, J=8.4 Hz, 2H), 7.07-7.11 (m, 2H), 7.46 (d, J=7.8 Hz, 2H).

5. 2-(4-(3',4'-dimethoxy-[1,1'-biphenyl]-4-yl)piperazin-1-yl)ethanol

Compound 8 (2 g, 4.4 mmol) was dissolved in THF (25 mL) and cooled to 0° C. TBAF (n-tetrabutylammonium fluoride) 1M in THF (8.76 mL, 8.76 mmol) was added at 0° C., and reaction stirred at room temperature for 2 h. After reaction was complete, saturated $NaHCO_3$ solution (50 mL) was added, and reaction mixture was extracted with $CH_2Cl_2$ (3×150 mL), which was then concentrated in vacuo. The resulting crude was purified by column chromatography using 0-5% methanol in $CH_2Cl_2$ to give compound 9 (1.34 g, 89%). $^1$H NMR ($CDCl_3$, 600 MHz): δ ppm 2.63 (t, J=5.4 Hz, 2H), 2.71 (t, J=5.4 Hz, 4H), 3.26 (t, J=4.8 Hz, 4H), 3.68 (t, J=5.4 Hz, 2H), 3.92 (s, 3H), 3.94 (s, 3H), 6.92 (d, J=8.4 Hz, 1H), 6.86 (d, J=9.0 Hz, 2H), 7.07-7.11 (m, 2H), 7.47 (d, J=9.0 Hz, 2H).

6. 2-(4-(3',4'-dimethoxy-[1,1'-biphenyl]-4-yl)piperazin-1-yl)acetaldehyde

A solution of DMSO (0.31 mL, 4.37 mmol) in $CH_2Cl_2$ (2 mL) was added into a round-bottom flask containing a stirring solution of oxalyl chloride (0.21 mL, 2.41 mmol) in $CH_2Cl_2$ (2 mL) at −78° C. The mixture was stirred for 0.5 h at the same temperature, and compound 9 (0.42 g, 1.23 mmol) in $CH_2Cl_2$ (3 mL) was added. The stirring of the reaction mixture was continued at −78° C. for another 0.5 h. Thereafter, $Et_3N$ (1.38 mL, 9.90 mmol) was added, and the reaction was allowed to warm to room temperature and continued for another 1 h. The reaction mixture was quenched by the addition of a saturated solution of $NaHCO_3$ at 0° C. and was extracted with $CH_2Cl_2$ (3×100 mL). The combined organic layer was dried over $Na_2SO_4$, and the solvent was removed in vacuo to produce the crude, which was purified by column chromatography using ethyl acetate to give compound 10 (0.379 g, 91%). $^1$H NMR (600 MHz, $CDCl_3$): δ ppm 2.73 (t, J=4.8 Hz, 4H), 3.27 (s, 2H), 3.30 (t, J=4.8 Hz, 4H), 3.92 (s, 3H), 3.94 (s, 3H), 6.92 (d, J=8.4 Hz, 1H), 6.98 (d, J=9.0 Hz, 2H), 7.07-7.11 (m, 2H), 7.47 (d, J=9.0 Hz, 2H), 9.76 (s, 1H).

Procedure A. 1a. 2-(4-(3',4'-dimethoxy-[1,1'-biphenyl]-4-yl)piperazin-1-yl)-N,N-diethylethanamine Into a stirring solution of amine 11a (38.4 μL, 0.37 mmol) in $CH_2Cl_2$ (10 mL) was added aldehyde 10 (127 mg, 0.37 mmol), and the mixture stirred for 1.5 h. $NaBH(OAc)_3$ (0.158 g, 0.75 mmol) was then added portion-wise. The reaction was stirred for 48 h at room temperature. The reaction mixture was quenched with a sat. $NaHCO_3$ solution at 0° C. and extracted with $CH_2Cl_2$ (3×30 mL). The combined organic layer was dried over $Na_2SO_4$, and solvent was removed under reduced pressure. The crude product was purified by column chromatography using 0-10% MeOH in $CH_2Cl_2$ to give compound 12a (127 mg, 86%). $^1$H NMR (600 MHz, $CDCl_3$): δ ppm 1.08 (t, J=7.2 Hz, 6H), 2.59-2.73 (m, 12H), 3.25 (t, J=5.4 Hz, 4H), 3.91 (s, 3H), 3.94 (s, 3H), 6.91 (d, J=8.4 Hz, 1H), 6.96 (d, J=8.4 Hz, 2H), 7.07-7.11 (m, 2H), 7.46 (d, J=9.0 Hz, 2H).

1b. N-(2-(4-(3',4'-dimethoxy-[1,1'-biphenyl]-4-yl)piperazin-1-yl)ethyl)-N-isopropylpropan-2-amine Aldehyde 10 (194 mg, 0.57 mmol), amine 11b (80.5 μL, 0.57 mmol), and $NaBH(OAc)_3$ (0.242 g, 1.14 mmol) in $CH_2Cl_2$ (10 mL) were reacted using procedure A, and the resulting crude was purified by column chromatography using 0-10% MeOH in $CH_2Cl_2$ to give compound 12b (117 mg, 48%). $^1$H NMR (600 MHz, $CDCl_3$): δ ppm 1.08 (bs, 12H), 2.45-2.81 (m, 8H), 2.98-3.16 (m, 2H), 3.25 (t, J=4.2 Hz, 4H), 3.92 (s, 3H), 3.94 (s, 3H), 6.91 (d, J=8.4 Hz, 1H), 6.97 (d, J=9.0 Hz, 2H), 7.07-7.10 (m, 2H), 7.46 (d, J=8.4 Hz, 2H).

1c. 2-(4-(3',4'-dimethoxy-[1,1'-biphenyl]-4-yl)piperazin-1-yl)-N-(4-fluorobenzyl)ethanamine Aldehyde 10 (185 mg, 0.54 mmol), amine 11c (61.7 μL, 0.54 mmol), and $NaBH(OAc)_3$ (0.23 g, 1.09 mmol) in $CH_2Cl_2$ (10 mL) were reacted using procedure A, and the resulting crude was purified by column chromatography using 0-10% MeOH in $CH_2Cl_2$ to give compound 12c (73 mg, 30%). $^1$H NMR (600 MHz, $CDCl_3$): δ ppm 2.59 (t, J=6.0 Hz, 6H), 2.75 (t, J=6.6 Hz, 2H), 3.22 (t, J=4.8 Hz, 4H), 3.81 (s, 2H), 3.91 (s, 3H), 3.94 (s, 3H), 6.91 (d, J=8.4 Hz, 1H), 6.97 (d, J=8.4 Hz, 2H), 7.02 (t, J=8.4 Hz, 2H), 7.07-7.11 (m, 2H), 7.31 (dd, J=8.4, 5.4 Hz, 2H), 7.46 (d, J=8.4 Hz, 2H).

Procedure B. 2a (D-690). 4'-[4-(2-Diethylamino-ethyl)-piperazin-1-yl]-biphenyl-3,4-diol (D-690)

Compound 12a (44 mg, 0.11 mmol) was treated with 48% hydrobromic acid (2.5 mL) and refluxed for 6 h. HBr was removed to obtain the residue, which was then dissolved in MeOH and filtered through cotton. The filtrate was concentrated and washed with ether for three times followed drying to give the hydrobromide salt of compound 13a (D-690) (63.5 mg, 89%). $^1$H NMR (600 MHz, $CD_3OD$): δ ppm 1.40 (t, J=7.2 Hz, 6H), 3.31-3.94 (m, 16H), 6.78 (d, J=7.8 Hz, 1H), 6.91 (d, J=8.4 Hz, 1H), 7.00 (d, J=2.4 Hz, 1H), 7.10-7.31 (m, 2H), 7.52 (d, J=8.4 Hz, 2H). Mp 198-200° C. Ana. ($C_{22}H_{38}Br_3N_3O_4$) C, H, N.

13b (D-687). 4'-[4-(2-Diisopropylamino-ethyl)-piperazin-1-yl]-biphenyl-3,4-diol (D-687)

Compound 2b (41 mg, 0.096 mmol) was treated with 48% hydrobromic acid (2.2 mL) and refluxed for 6 h by following procedure B. The crude was washed with ether for three times followed drying to give the hydrobromide salt of compound 13b (D-687) (49.6 mg, 75%). $^1$H NMR (600 MHz, $CD_3OD$): δ ppm 1.46 (s, 6H), 1.47 (s, 6H), 3.34-3.90 (m, 14H), 6.79 (d, J=7.8 Hz, 1H), 6.90 (d, J=8.4 Hz, 1H), 7.00 (s, 1H), 7.18-7.28 (m, 2H), 7.51 (d, J=8.4 Hz, 2H). Mp 168-171° C. Ana. ($C_{24}H_{43}Br_3N_3O_{4.5}$) C, H, N.

2c (D-688). 4'-{4-[2-(4-Fluoro-benzylamino)-ethyl]-piperazin-1-yl}-biphenyl-3,4-diol (D-688)

Compound 12c (63 mg, 0.14 mmol) was treated with 48% hydrobromic acid (3.2 mL) and refluxed for 6 h by following procedure B. The crude was washed with ether for three times followed drying to give the hydrobromide salt of compound 13e (D-688) (80.5 mg, 82%). $^1$H NMR (600 MHz, $CD_3OD$): δ ppm 3.59-3.72 (m, 12H), 4.39 (s, 2H), 6.82 (d, J=7.8 Hz, 1H), 6.93 (d, J=6.6 Hz, 1H), 7.03 (d, J=1.8 Hz, 1H), 7.20-7.25 (m, 4H), 7.53 (d, J=9.0 Hz, 2H), 7.69-7.71 (m, 2H). Mp 200-203° C. Ana. ($C_{25}H_{35}Br_3FN_3O_4$) C, H, N.

Modulation of Alpha Synuclein Study

We assessed the ability of our compounds, D-687 and D-688, to alter aggregation and cytotoxicity after co-incubating αSN with these drugs for 6 days followed by evaluation of ThT fluorescence activity and cell viability experiment with the PC12 cells. A total inhibition of ThT activity was observed at day 6 in the presence of these compounds compared to □SN alone, indicating alteration of the aggregation process in the presence of drugs. In order to maintain identical condition, cellular viability was determined by using samples from various experiments diluted to maintain a final concentration of 10 μM of αSN and 20 μM of drugs. Treatment with pre-aggregated αSN alone showed a reduction of cell viability by ~40%

Figure 2A:
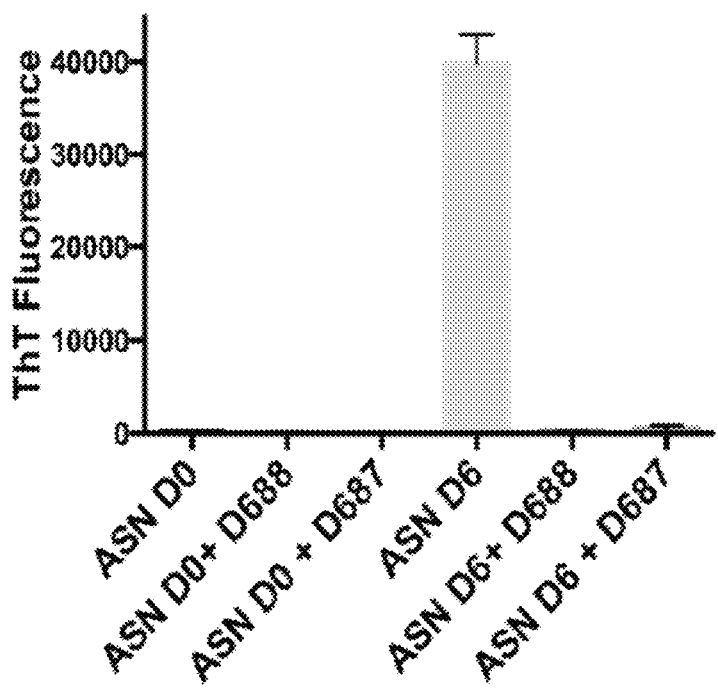
FIGS. 2A-B. (A) Inhibition of aSN fibrillization by D-687 and D-688. The drugs were incubated with aSN over a period of six days and the fibrilization was measured by ThT fluorescence assay. Data Values shown are means±SEMs of three independent experiments. (B) PC12 cells were treated with 10 μM prefabricated aSN aggregates formed in presence of drugs collected at day 0 and day 6. Values shown are means±SEMs of three independent experiments performed in 4-6 replicates. One way ANOVA analysis followed by Tukey's Multiple Comparison post hoc test were performed. (*p<0.01 compared to the control).
Figure 2B:
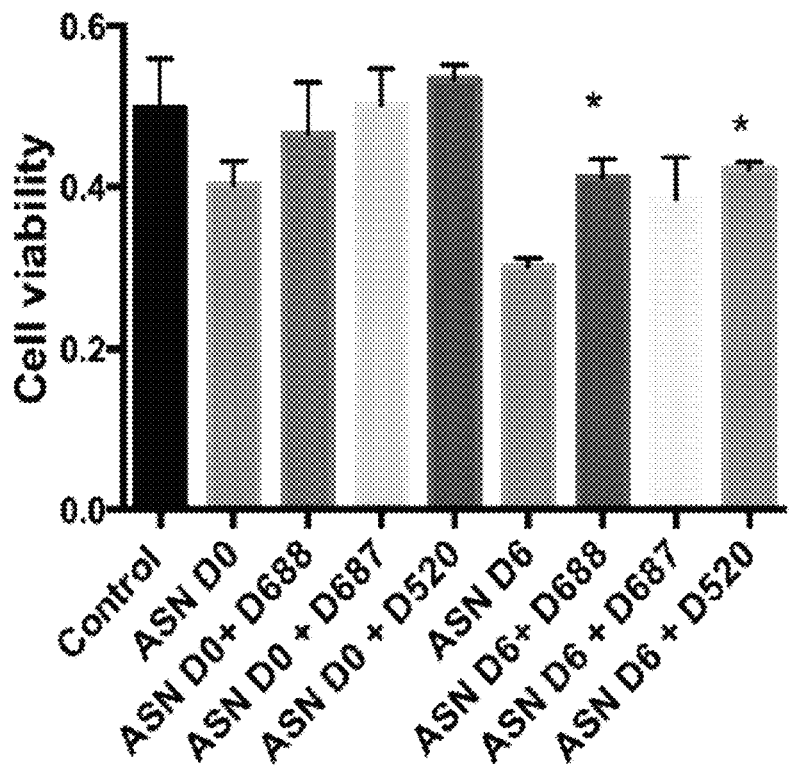

FIG. 2 provides (A) Inhibition of aSN fibrillization by D-687 and D-688. The drugs were incubated with aSN over a period of six days and the fibrilization was measured by ThT fluorescence assay. Data Values shown are means±SEMs of three independent experiments. (B) PC12 cells were treated with 10 μM prefabricated αSN aggregates formed in presence of drugs collected at day 0 and day 6. Values shown are means±SEMs of three independent experiments performed in 4-6 replicates. One way ANOVA analysis followed by Tukey's Multiple Comparison post hoc test were performed. (*$p<0.01$ compared to the control).

Modulation of Amyloid Beta Aggregation:

We next evaluated effect of our compounds on modulation of aggregation and disaggregation activity of $A\beta_{1-42}$ peptide.

Figure 3A:
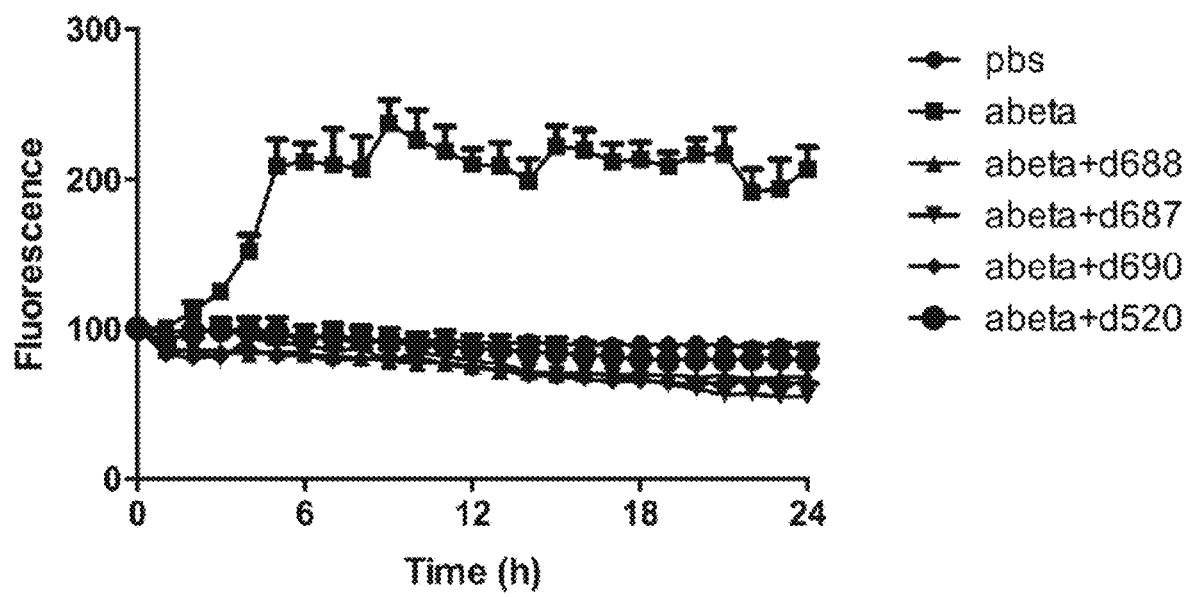
FIGS. 3A and 3B. Inhibition and dissociation of $A\beta_{1-42}$ oligomer formation by: a) ThT fluorescence of $A\beta_{1-42}$ (10 μM) with or without incubation with test compounds (20 μM) for 24 h. The ThT fluorescence of $A\beta_{1-42}$ at 0 h was taken as 100%. b) $A\beta_{1-42}$ fibrils (10 μM) were incubated with test compounds (20 μM) for a period of 24 h. The ThT fluorescence of $A\beta_{1-42}$ aggregates at 0 h was considered as 100%
Figure 3B:
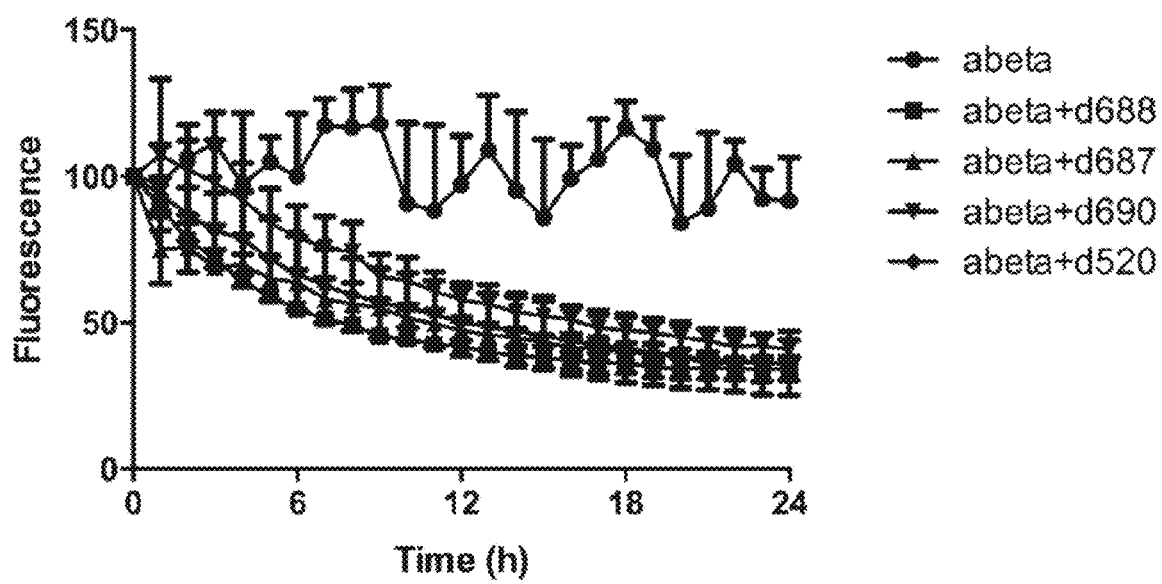
Figure 4:
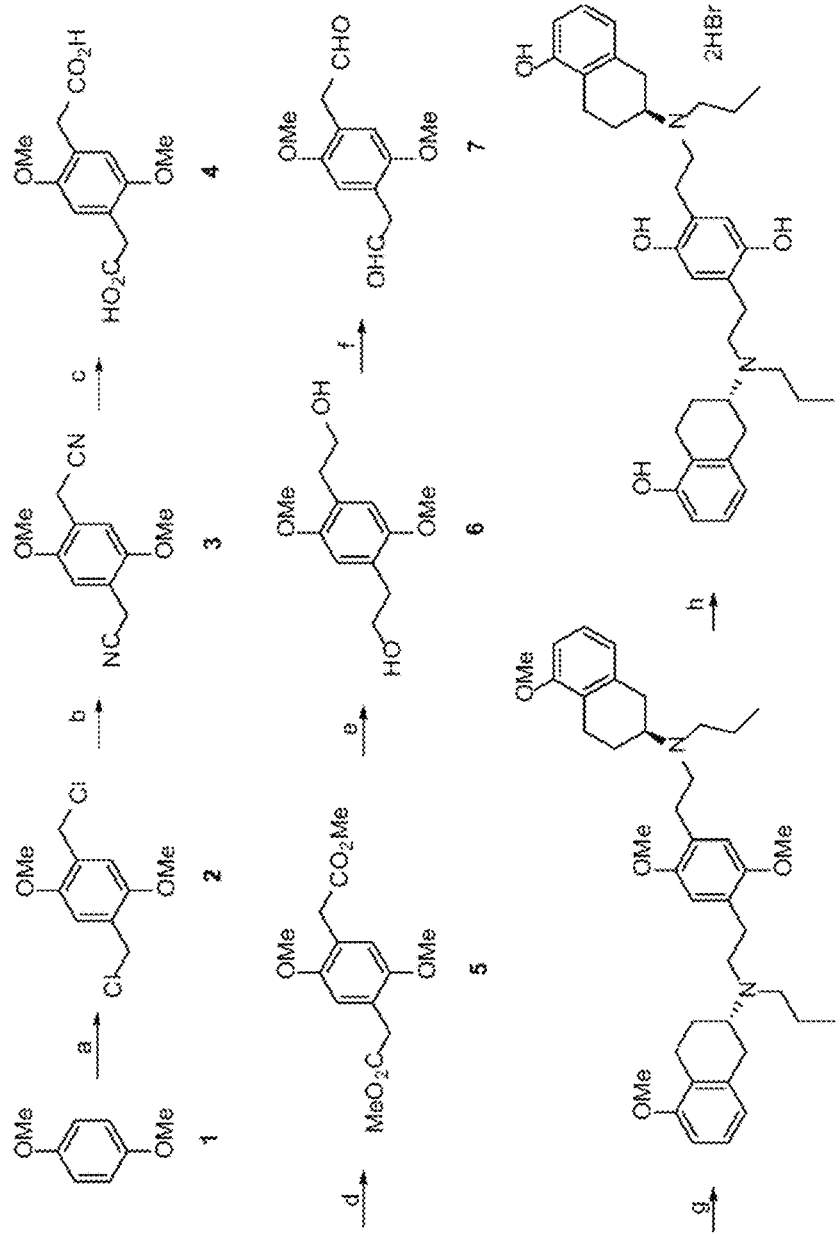
FIG. 4. Synthetic Scheme 2 for compounds that are useful for treating a neurodegenerative disease.

FIGS. 3A and 3B show inhibition and dissociation of $A\beta_{1-42}$ oligomer formation by: a) ThT fluorescence of $A\beta_{1-42}$ (10 μM) with or without incubation with test compounds (20 μM) for 24 h. The ThT fluorescence of $A\beta_{1-42}$ at 0 h was taken as 100%. b) $A\beta_{1-42}$ fibrils (10 μM) were incubated with test compounds (20 μM) for a period of 24 h. The ThT fluorescence of $A\beta_{1-42}$ aggregates at 0 h was considered as 100%

Similar to the effect of the drugs on α-syn, interaction of compounds with $A\beta_{1-42}$ peptide clearly indicated a significant effect in inhibiting aggregation in a time dependent manner as indicated by decrease in ThT activity (FIG. 3a). Similarly, test compounds were able to decrease ThT activity of preformed Aβ aggregates in a time dependent manner, reflecting its effect in disrupting structure of aggregates (FIG. 3b). On the other hand, incubation of aggregates itself led to a gradual increase in ThT activity (FIG. 3b). Therefore, test compounds exhibited dual activity in inhibiting association of $A\beta_{1-42}$ to form aggregates and in dissociating the formed aggregates.

Conclusion: The overall results indicate the compounds D687, D688 and D690 potently inhibited aggregation of aSN protein and $A\beta_{1-42}$ peptide and disaggregate $A\beta_{1-42}$.

II. Scheme 2

1,4-Bis(chloromethyl)-2,5-dimethoxybenzene (2)

Paraformaldehyde (3.3 g, 108.6 mmol) was added to a slurry of compound 1 (5.0 g, 36.2 mmol) in conc. HCl (15 mL) and acetic acid (15 mL) at rt under inert gas atmosphere. The mixture was sonicated for 2 h. The mixture was filtered and the solid was washed with hexane (3×50 mL) followed by acetone (15 mL). The crude product was purified by column chromatography using 5% ethyl acetate in hexane to afford compound 2 (5.53 g, 23.53 mmol, 65%) as white solid. $^1$H NMR (600 MHz, CDCl$_3$): δ 6.92 (s, 2H), 4.63 (s, 4H), 3.85 (s, 6H).

2,2'-(2,5-Dimethoxy-1,4-phenylene)diacetonitrile (3)

To a mechanically stirred suspension of NaCN (3.45 g, 70.46 mmol) in anhydrous dimethylsulfoxide was added in small portions of 2 (7.11 g, 30.24 mmol). The reaction mixture was stirred at 50° C. for 1 h. Temperature was increased to 85° C. and the reaction mixture was allowed to stir at that temperature for additional 5 minutes. The mixture was cooled to rt. The reaction mixture was diluted with water (100 mL) and extracted with ethyl acetate (3×150 mL). The combined organic layer was washed with water, brine, dried over Na$_2$SO$_4$, and solvent was removed under vacuum. Crude product was purified by column chromatography using 20% ethyl acetate in hexane to give compound 3 (4.57 g, 21.17 mmol, 70%) as white solid. $^1$H NMR (600 MHz, CDCl$_3$): δ 6.92 (s, 2H), 3.85 (s, 6H), 3.70 (s, 4H).

2,2'-(2,5-Dimethoxy-1,4-phenylene)diacetic acid (4)

To a suspension of compound 3 (0.40 g, 1.85 mmol) in conc. HCl (10 mL) was added acetic acid (1 mL). The mixture was allowed to stir at 100° C. for 3 h. After completion of the reaction as indicated by TLC, the mixture was cooled to rt. The mixture of acids was removed under low pressure. The crude residue was extracted with ethyl acetate (70 mL) and washed with water (3×20 mL). The organic layer was washed with brine and dried over Na$_2$SO$_4$. The solvent was removed under vacuum. Crude product was purified by column chromatography using 10% methanol in dichloromethane to give compound 4 (0.28 g, 1.11 mmol, 60%) as brown solid. $^1$H NMR (600 MHz, d$_6$-DMSO): δ 12.14 (brs, 2H), 6.82 (s, 2H), 3.66 (s, 6H), 3.65 (s, 4H).

Dimethyl 2,2'-(2,5-dimethoxy-1,4-phenylene)diacetate (5)

To a suspension of the acid 4 (1.0 g, 3.93 mmol) in methanol (25 mL) was slowly added thionylchloride (4.85 mL, 66.86 mmol) at 0° C. The mixture was allowed to stir at that temperature for 1 h. Then the reaction temperature was gradually increased to rt and the stirring was continued for 24 h. Solvent and excess reagents were removed under low pressure. The crude residue was extracted with ethyl acetate (120 mL) and washed with saturated aqueous NaHCO$_3$ solution (40 mL). The organic layer was washed with water (3×30 mL), brine and dried over Na$_2$SO$_4$. The solvent was removed under vacuum. Crude product was purified by column chromatography using 3% methanol in dichloromethane to give compound 5 (0.61 g. 2.16 mmol, 55%) as white solid. $^1$H NMR (600 MHz, CDCl$_3$): δ 6.74 (s, 2H), 3.77 (s, 6H), 3.68 (s, 6H), 3.61 (s, 4H).

2,2'-(2,5-Dimethoxy-1,4-phenylene)diethanol (6)

To a stirring solution of the ester 5 (0.56 g, 2.0 mmol) in THF (20 mL) was added LiAlH$_4$ (0.30 g, 8.0 mmol) in portions at 0° C. under inert gas atmosphere and the stirring was continued for 1 h. The reaction temperature was increased to rt and the mixture was allowed to stir for overnight. The reaction was quenched with the addition of water (3 mL) followed by 2 N aqueous NaOH (3-5 mL) at 0° C. The mixture was filtered through celite and the solid residue was washed with THF (2×20 mL) followed by hot ethylacetate (40 mL). The combined solution was evaporated under vacuum. Crude product was purified by column chromatography using 3% methanol in dichloromethane to give compound 6 (0.25 g, 1.10 mmol, 55%) as white solid.

¹H NMR (600 MHz, CDCl₃): δ 6.71 (s, 2H), 3.82 (t, J=6.6 Hz, 4H), 3.78 (s, 6H), 2.87 (t, J=6.6 Hz, 4H).

2,2'-(2,5-Dimethoxy-1,4-phenylene)diacetaldehyde (7)

To a stirring solution of 6 (50 mg, 0.22 mmol) in DCM (10 mL) was added Dess-Martin periodinane (280 mg, 0.66 mmol) at rt. After stirring the reaction mixture for 4 h the volume of the mixture was reduced to half under low pressure. It was then passed through celite and the solid was washed with DCM (2×7 mL). The combined filtrate was evaporated to produce a solid residue which was purified by column chromatography using 25% ethylacetate in hexane to give compound 7 (29 mg, 0.13 mmol, 60%). ¹H NMR (600 MHz, CDCl₃): δ 9.68 (t, J=1.8 Hz, 2H), 6.71 (s, 2H), 3.77 (s, 6H), 3.65 (d, J=1.8 Hz, 4H).

(2S,2'S)—N,N'-((2,5-dimethoxy-1,4-phenylene)bis(ethane-2,1-diyl))bis(5-methoxy-N-propyl-1,2,3,4-tetrahydronaphthalen-2-amine) (9)

Into a stirring solution of compound 7 (47 mg, 0.211 mmol) in DCM (6 mL), (S)-5-methoxy-N-propyl-1,2,3,4-tetrahydronaphthalen-2-amine (8) (93 mg, 0.422 mmol) was added at room temperature. The reaction mixture was stirred for 1 h, and then NaBH(OAc)₃ (161 mg, 0.759 mmol) was added into the solution. After stirring for 40 h, saturated solution of NaHCO₃ (6 mL) was added into the reaction mixture and the compound was extracted with DCM (3×10 mL). The combined organic layer was washed with water and brine and finally purified by silica gel column chromatography (60% EtOAc in hexane) to yield compound 9 (33 mg, 0.05 mmol, 25%). ¹H NMR (600 MHz, CDCl₃): δ 7.08 (dd, J₁=8.4 Hz, J₂=7.8 Hz, 2H), 6.71 (d, J=7.8 Hz, 2H), 6.66 (s, 2H), 6.65 (d, J=8.4 Hz, 2H), 3.80 (s, 6H), 3.77 (s, 6H), 3.01-2.86 (m, 6H), 2.77-2.72 (m, 8H), 2.56-2.50 (m, 6H), 2.11 (m, 2H), 1.66-1.55 (m, 8H), 0.91 (t, J=7.2 Hz, 6H). ¹³C NMR (150 MHz, CDCl₃): δ 157.2, 151.3, 138.2, 127.4, 126.1, 125.3, 121.6, 113.5, 106.8, 56.8, 56.1, 55.2, 52.7, 51.1, 32.5, 30.5, 25.8, 23.8, 22.1, 12.0.

2,5-Bis(2-(((S)-5-hydroxy-1,2,3,4-tetrahydronaphthalen-2-yl)(propyl)amino)ethyl)benzene-1,4-diol (10)

A mixture of compound 9 (30 mg, 0.048 mmol) and 48% aqueous HBr (6 mL) was refluxed for 6 h. The reaction mixture was then evaporated to dryness in vacuum. The crude mixture was then washed with diethyl ether to afford compound 10 as a brown solid (31 mg, 0.042 mmol, 88%). ¹H NMR (600 MHz, CD₃OD): δ 6.96 (t, J=7.8 Hz, 2H), 6.70-6.69 (m, 2H), 6.63-6.60 (m, 4H), 3.79-3.76 (m, 2H), 3.52-3.46 (m, 2H), 3.39-3.32 (m, 4H), 3.24-3.16 (m, 4H), 3.09-2.95 (10H), 2.66-2.56 (m, 2H), 2.40-2.32 (m, 2H), 1.89-1.78 (m, 6H), 1.05 (t, J=7.2 Hz, 8H).

Figure 5:
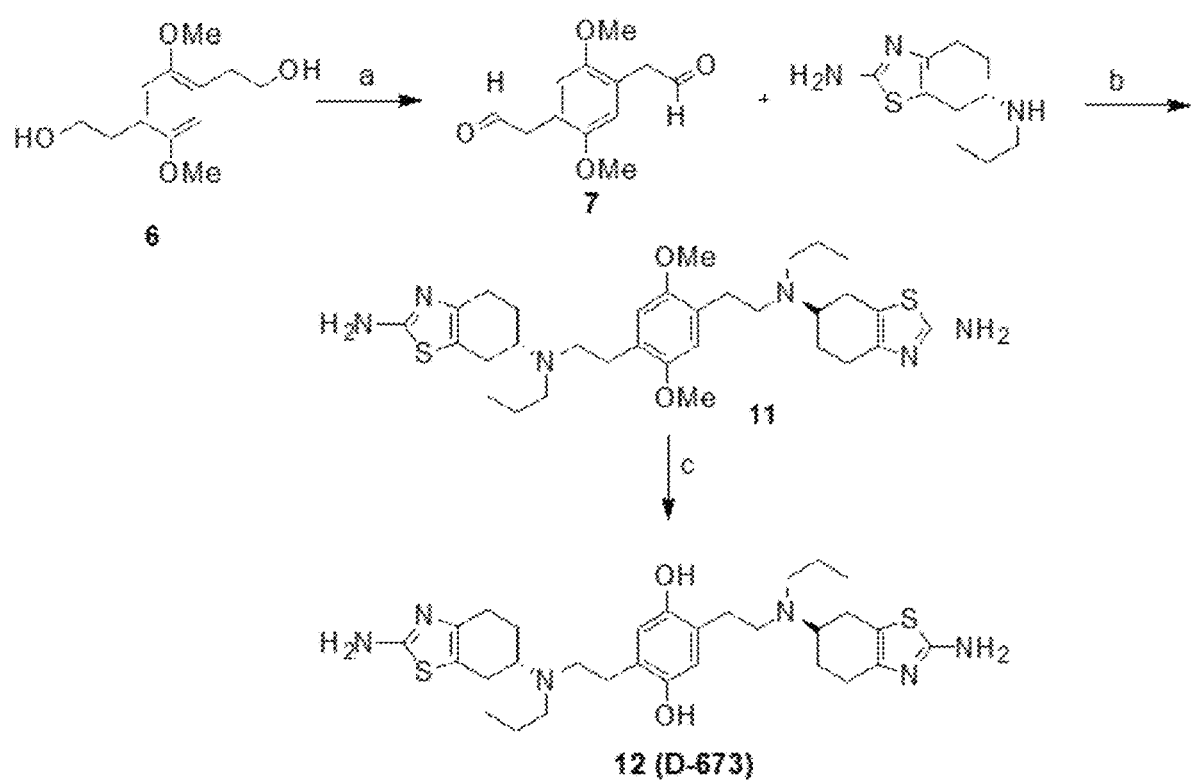
FIG. 5. Synthetic Scheme 3 for compounds that are useful for treating a neurodegenerative disease.

C. Scheme 3 (FIG. 5)

2,2'-(2,5-Dimethoxy-1,4-phenylene)diacetaldehyde (7)

To a stirring suspension of alcohol 6 (0.12 g, 0.53 mmol) in CH₂Cl₂ (10 mL) was added Dess-Martin periodinane (0.675 g, 1.59 mmol) at room temperature. After stirring the reaction mixture for 4 h, it was filtered through a pad of celite, washed with CH₂Cl₂ and the combined filtrate was evaporated to produce a solid residue. The crude product was purified by silica gel column chromatography (hexane:ethyl acetate=3:1) to give aldehyde 7 (0.1 g, 85%). The purified aldehyde was used immediately for next step. ¹H NMR (600 MHz, CDCl₃): δ 9.69 (s, 1H), 6.73 (s, 2H), 3.78 (s, 6H), 3.66 (d, J=1.8 Hz, 4H).

2,5-bis(2-(((S)-2-amino-4,5,6,7-tetrahydrobenzo[d]thiazol-6-yl)(propyl)amino)-ethyl)benzene-1,4-diol (11)

Into a stirring solution of aldehyde 7 (0.09 g, 0.41 mmol) in CH₂Cl₂ (10 mL) was added (S)—N⁶-propyl-4,5,6,7-tetrahydrobenzo[d]thiazole-2,6-diamine (0.154 g, 0.73 mmol). After the mixture was stirred for 1.5 h, NaBH(OAc)₃ (0.343 g, 1.62 mmol) was added portion wise and the mixture was stirred for 48 h at room temperature. The reaction mixture was quenched with a saturated solution of NaHCO₃ at 0° C. and extracted with CH₂Cl₂ (3×40 mL). The combined organic layer was dried over Na₂SO₄, and the solvent was removed under reduced pressure. Crude product was purified by column chromatography (EtOAc/MeOH 8:1) to afford compound 11 (0.085 g, 34%). ¹H NMR (600 MHz, CDCl₃): δ 6.65 (s, 2H), 5.19 (bs, 4H), 3.77 (s, 6H), 3.13-3.07 (m, 2H), 2.73-2.67 (m, 12H), 2.59-2.49 (m, 8H), 2.01-1.99 (m, 2H), 1.74-1.68 (m, 2H), 1.54-1.48 (m, 4H), 0.90 (t, J=7.2 Hz, 6H); ¹³C NMR (150 MHz, CDCl₃): δ 165.91, 151.21, 144.84, 127.20, 117.10, 113.45, 60.41, 57.79, 56.08, 52.91, 51.24, 30.71, 26.48, 25.94, 25.12, 22.15, 14.18, 11.90; [α]$_D^{25}$=−55.2 (c=1.0 in CH₂Cl₂).

2,5-bis(2-(((S)-2-amino-4,5,6,7-tetrahydrobenzo[d]thiazol-6-yl)(propyl)amino)-ethyl)benzene-1,4-diol (12) (D-673)

A mixture of compound 11 (0.075 g, 0.12 mmol) and 48% aqueous HBr (15 mL) was refluxed at 130° C. for 5 h. The reaction mixture was evaporated to dryness, washed with ether followed by vacuum drying to yield HBr salt of 12 (0.105 g, 95%). ¹H NMR (600 MHz, CD₃OD): δ 6.77 (s, 2H), 4.03 (s, 2H), 3.55-3.33 (m, 8H), 3.27-3.23 (m, 2H), 3.14 (t, J=10.2 Hz, 2H), 3.04 (t, J=7.8 Hz, 4H), 3.00-2.94 (m, 2H), 2.78 (bs, 4H), 2.47-2.41 (m, 2H), 2.18-2.11 (m, 2H), 1.94-1.83 (m, 4H), 1.04 (t, J=7.2 Hz, 6H); ¹³C NMR (150 MHz, CD₃OD): δ 173.95, 151.96, 136.64, 126.43, 120.98, 115.79, 63.10, 62.86, 57.37, 56.82, 54.90, 52.45, 29.99, 27.01, 26.16, 25.54, 22.26, 13.99; [α]$_D^{25}$=−42.0 (c=1.0 in CH₃OH); Anal. Calcd for $C_{30}H_{51}Br_5N_6O_3S_2$: C, 35.77; H, 5.10; N, 8.34. Found: C, 36.08; H, 5.42; N, 8.27.

TABLE 1

Inhibition constants determined by competition experiments assessing [³H]spiroperidol binding to cloned $D_{2L}$ and $D_3$ receptors expressed in HEK-293 cells[a]

| Compound | $K_i$ (nM) | | $D_{2L}/D_3$ |
|---|---|---|---|
| | $D_{2L}$, [³H]spiroperidol | $D_3$, [³H]spiroperidol | |
| (−)-5-OH-DPAT | 153 ± 32 | 2.07 ± 0.38 | 74 |
| 10 | 7.62 ± 2.5 | 5.22 ± 1.22 | |
| 12 (D-673) | 54.7 ± 3.3 | 6.87 ± 0.11 | |

[a]Results are the mean ± SEM of 3-6 experiments, each performed in triplicate.

TABLE 2

Stimulation of [$^{35}$S]GTPγS binding to cloned human
D$_2$ and D$_3$ receptors expressed in CHO cells[a]

| | hCHO-D$_2$ | | hCHO-D$_3$ | | |
|---|---|---|---|---|---|
| Compound | [$^{35}$S] GTPγS EC$_{50}$ (nM) | E$_{max}$(%) | [$^{35}$S]GTPγS EC$_{50}$ (nM) | E$_{max}$(%) | D$_2$/D$_3$ |
| Dopamine (DA) | 376 ± 39 | 100 | 7.26 ± 0.21 | 100 | 52 |
| (−)-5-OH-DPAT | 41 ± 6 | 80 ± 4 | 0.63 ± 0.08 | 75 ± 4 | 65 |
| 10 | 7.69 ± 1.08 | 59.1 ± 5.6 | 1.53 (4) ± 0.311 | 83.7 ± 5.3 | |

[a]EC$_{50}$ is the concentration producing half maximal stimulation. For each compound, maximal stimulation (E$_{max}$) is expressed as a percent of the E$_{max}$ observed with 1 mM (D$_2$) or 100 μM (D$_3$) of the full agonist DA (E$_{max}$, %). Results are the mean ± SEM for 3-6 experiments, each performed in triplicate.

D. Scheme 4 (FIG. 6)

Synthesis of D-679

N-(2,5-Dioxo-tetrahydro-furan-3-yl)-2,2,2-trifluoro-acetamide (1)

Trifluoroacetic anhydride (13.12 mL, 93.91 mmol) was added to D-aspartic acid (5.0 g, 37.57 mmol) at −60° C. and stirred for 10 min. The reaction mixture was allowed to warm to room temperature and then to 40° C. during which a vigorous exothermic reaction took place. Trifluoroacetic acid (10 mL) was added next and the reaction mixture was stirred under refluxing condition for 2 h. After cooling, petroleum ether was added and the solid thus formed was collected by filtration, washed successively with petroleum ether and ether and finally dried under vacuum to afford compound 1 (7.7 g, 97%). $^1$H NMR (600 MHz, Acetone-D$_6$): δ 9.41 (bs, 1H), 5.30-5.26 (m, 1H), 3.53 (q, J=10.2 Hz, 1H), 3.27 (dd, J=12.0, 6.6 Hz, 1H).

4-(3,4-Dimethoxy-phenyl)-4-oxo-2-(2,2,2-trifluoro-acetylamino)-butyric acid (2)

To a stirring suspension of compound 1 (4.0 g, 18.95 mmol) and AlCl$_3$ (6.3 g, 47.37 mmol) in CH$_2$Cl$_2$ (90 mL), veratrole (3.62 mL, 28.42 mmol) was added and the reaction mixture was stirred at room temperature for 4 days. 6M HCl was added to the reaction vessel and the layers were separated. Aqueous layer was extracted with ether (3×50 mL) and the combined organic portions were dried over Na$_2$SO$_4$, filtered and evaporated under reduced pressure. The crude material was purified by silica gel column chromatography (hexane:EtOAc=1:1) to give compound 2 (5.3 g, 80%). $^1$H NMR (600 MHz, CDCl$_3$): δ 7.61 (bs, 1H), 7.58 (d, J=8.4 Hz, 1H), 7.48 (s, 1H), 6.92 (d, J=8.4 Hz, 1H), 5.02-5.00 (m, 1H), 3.97 (s, 3H), 3.93 (s, 3H), 3.89-3.86 (m, 1H), 3.58 (dd, J=14.4, 4.2 Hz, 1H).

4-(3,4-Dimethoxy-phenyl)-2-(2,2,2-trifluoro-acety-lamino)-butyric acid (3)

Triethylsilane (9.7 mL, 60.7 mmol) was added to a magnetically stirred solution of keto acid 2 (5.3 g, 15.18 mmol) in trifluoroacetic acid (22.5 mL, 303.5 mmol). This solution was boiled under reflux under N$_2$ for 2 h after which it was cooled and carefully neutralized to pH 8 with NaHCO$_3$ solution at 0° C. The aqueous solution was washed twice with Et$_2$O and acidified (pH<5) by the dropwise addition of 6N HCl at 0° C. The product was extracted with Et$_2$O (3×30 mL), the organic layers were dried over MgSO$_4$, and the ether was removed by rotary evaporation to yield a yellow oil, which solidified on standing. This solid was recrystallized from EtOAc/hexane to afford carboxylic acid 3 (4.7 g, 92%). $^1$H NMR (600 MHz, CDCl$_3$): δ 6.81 (d, J=8.4 Hz, 1H), 6.74-6.71 (m, 2H), 6.70 (d, J=1.2 Hz, 1H), 4.73-4.70 (m, 1H), 3.87 (s, 3H), 3.86 (s, 3H), 2.68 (t, J=7.2 Hz, 2H), 2.37-2.31 (m, 1H), 2.21-2.15 (m, 1H).

N-(6,7-Dimethoxy-1-oxo-1,2,3,4-tetrahydro-naph-thalen-2-yl)-2,2,2-trifluoro-acetamide (4)

To an ice-cooled solution of compound 3 (4.5 g, 13.42 mmol) in 40 mL of CH$_2$Cl$_2$ was added solid PCl$_5$ (3.35 g, 16.11 mmol). Stirring was continued for 1 h at 0° C., and SnCl$_4$ (3.14 mL, 26.84 mmol) was added. The mixture was stirred for 0.5 h at 0° C. and then allowed to warm to room temperature and stirred for an additional 4 h. The mixture was poured into ice water and vigorously stirred for 15 min. The layers were separated, and the aqueous phase was extracted with CH$_2$Cl$_2$ (3×50 mL). The organic portions were dried over MgSO$_4$ and rotary evaporated to furnish white solid, which was purified by silica gel column chromatography (hexane:EtOAc=3:2) to give colorless tetralone 4 (2.5 g, 59%). $^1$H NMR (600 MHz, CDCl$_3$): δ 7.58 (bs, 1H), 7.46 (dd, J=3.6, 1.2 Hz, 1H), 6.69 (s, 1H), 4.58-4.54 (m, 1H), 3.96 (s, 3H), 3.93 (s, 3H), 3.26-3.20 (m, 1H), 2.99-2.96 (m, 1H), 2.89-2.85 (m, 1H), 1.95 (dq, J=9.0, 4.8 Hz, 1H).

N-(6,7-Dimethoxy-1,2,3,4-tetrahydro-naphthalen-2-yl)-2,2,2-trifluoro-acetamide (5)

Triethylsilane (4.53 mL, 28.37 mmol) was added to a solution of compound 4 (2.25 g, 7.09 mmol) in 17.5 mL (141.84 mmol) of BF$_3$.Et$_2$O, and the resulting solution was stirred at room temperature under N$_2$ for 48 h. After basification of the mixture by addition to saturated NaHCO$_3$, the layers were separated, and the product was extracted with Et$_2$O (3×50 mL). The combined organic layers were dried over Na$_2$SO$_4$ and concentrated on a rotary evaporator. The crude residue was purified by silica gel column chromatography (hexane:EtOAc=7:3) to afford compound 5 (1.65 g, 77%). $^1$H NMR (600 MHz, CDCl$_3$): δ 6.59 (s, 1H), 6.55 (s, 1H), 6.34 (bs, 1H), 4.37-4.30 (m, 1H), 3.85 (s, 3H), 3.84 (s, 3H), 3.11 (dd, J=11.4, 4.8 Hz, 1H), 2.90-2.85 (m, 1H), 2.83-2.78 (m, 1H), 2.67 (dd, J=8.4, 7.8 Hz, 1H), 2.11-2.06 (m, 1H), 1.91-1.85 (m, 1H).

6,7-Dimethoxy-1,2,3,4-tetrahydro-naphthalen-2-ylamine (6)

To a stirred suspension of K$_2$CO$_3$ (1.37 g, 9.9 mmol) in 30 mL of MeOH containing 1.5 mL of H$_2$O was added trifluoroacetamide 5 (1.0 g, 3.3 mmol), and the mixture was boiled under reflux for 4 h. The mixture was allowed to cool to room temperature, and the undissolved K$_2$CO$_3$ was removed by filtration through a cotton plug. The filtrate was concentrated in vacuo, and the dark residue was diluted with water. The product was extracted with EtOAc (3×40 mL), the organic layers were dried over Na$_2$SO$_4$ and the volatiles were removed by rotary evaporator to furnish compound 6 (0.65 g, 95%). $^1$H NMR (600 MHz, CD$_3$OD): δ 6.62 (s, 1H), 6.60 (s, 1H), 4.87 (bs, 2H), 3.75 (s, 6H), 3.03-2.99 (m, 1H), 2.88 (dd, J=10.8, 4.8 Hz, 1H), 2.79-2.72 (m, 2H), 2.45 (dd, J=9.6, 6.0 Hz, 1H), 2.00-1.95 (m, 1H), 1.55-1.49 (m, 1H).

N-(6,7-Dimethoxy-1,2,3,4-tetrahydro-naphthalen-2-yl)-2-nitro-benzenesulfonamide (7)

2-Nitrobenzenesulfonyl chloride (0.64 g, 2.89 mmol) was dissolved in 20 mL of THF, and the solution was cooled to approximately −10° C. Et$_3$N (1.82 mL, 13.03 mmol) and compound 6 (0.6 g, 2.89 mmol) were added and the resulting suspension was heated during mixing to approximately 25° C., and allowed to react for 1.5 h. Precipitated triethylammonium chloride was filtered off, and the filtrate was concentrated. Water was added and extracted with EtOAc (3×30 mL). The combined organic layer was dried using Na$_2$SO$_4$, and the solvent was removed under reduced pressure to obtain sulfonamide 7 (1.05 g, 93%). $^1$H NMR (600 MHz, CDCl$_3$): δ 8.21-8.19 (m, 1H), 7.90-7.88 (m, 1H), 7.78-7.74 (m, 2H), 6.54 (s, 1H), 6.41 (s, 1H), 5.40 (d, J=7.2 Hz, 1H), 3.83 (s, 3H), 3.80 (s, 3H), 2.95-2.91 (m, 1H), 2.81-2.74 (m, 2H), 2.69-2.65 (m, 1H), 2.01-1.97 (m, 1H), 1.83-1.77 (m, 1H); $[α]_D^{25}$=+76.6 (c=1.0 in CH$_2$Cl$_2$).

N-(6,7-Dimethoxy-1,2,3,4-tetrahydro-naphthalen-2-yl)-2-nitro-N-propyl-benzenesulfonamide (8)

To a stirred suspension of 7 (1.0 g, 2.55 mmol) and potassium carbonate (2.47 g, 17.84 mmol) in acetonitrile (25 mL), 1-bromopropane (0.69 mL, 7.65 mmol) was added and the reaction mixture was stirred at 40° C. for 48 h. The reaction mixture was cooled to room temperature, filtered off and the filtrate was evaporated under reduced pressure. The crude product was purified by silica gel column chromatography (hexane:EtOAc=7:3) to afford compound 8 (0.99 g, 89%). $^1$H NMR (600 MHz, CDCl$_3$): δ 8.09 (dd, J=6.0, 1.8 Hz, 1H), 7.71-7.66 (m, 2H), 7.63 (dd, J=6.0, 1.8 Hz, 1H), 6.55 (s, 1H), 6.50 (s, 1H), 4.12-4.06 (m, 1H), 3.83 (s, 3H), 3.82 (s, 3H), 3.28 (t, J=7.8 Hz, 2H), 2.96-2.78 (m, 4H), 2.01-1.98 (m, 1H), 1.87-1.80 (m, 1H), 1.74-1.64 (m, 2H), 0.90 (t, J=7.2 Hz, 3H); $[α]_D^{25}$=+75.4 (c=1.0 in CH$_2$Cl$_2$).

(6,7-Dimethoxy-1,2,3,4-tetrahydro-naphthalen-2-yl)-propyl-amine (9)

Into a mixture of potassium carbonate (1.63 g, 11.81 mmol) in 20 mL of DMF, thioglycolic acid (0.47 mL, 6.56 mmol) was added slowly at 0° C. The mixture was stirred at room temperature for approximately 1 h, followed by addition of compound 8 (0.57 g, 1.31 mmol, in 10 mL of DMF). The reaction mixture was heated during stirring to about 50° C. and allowed to react for an additional 15 h, after which it was quenched by addition of 1N NaOH and extracted with EtOAc (4×25 mL). The combined organic layer was dried using Na$_2$SO$_4$, and the solvent was concentrated under reduced pressure. The crude product was purified by silica gel column chromatography (0-10% MeOH in CH$_2$Cl$_2$) to give compound 9 (0.22 g, 67%). $^1$H NMR (600 MHz, CDCl$_3$): δ 6.56 (d, J=5.4 Hz, 2H), 3.84 (s, 3H), 3.82 (s, 3H), 2.99-2.91 (m, 2H), 2.82-2.76 (m, 2H), 2.71 (t, J=7.8 Hz, 2H), 2.60-2.56 (m, 2H), 2.08-2.06 (m, 1H), 1.66-1.55 (m, 3H), 0.95 (t, J=7.2 Hz, 3H); $[α]_D^{25}$=+68.6 (c=1.0 in CH$_2$Cl$_2$).

Procedure A. (4-{[(5-Methoxy-1,2,3,4-tetrahydro-naphthalen-2-yl)-propyl-carbamoyl]-methyl}-phenyl)-acetic acid (10)

To a solution of 1,4-phenylenediacetic acid (1.0 g, 5.15 mmol) in DMF (20 mL) were added EDC (0.296 g, 1.54 mmol), HOBt (0.21 g, 1.54 mmol) and Et$_3$N (0.25 mL, 1.80 mmol) and the resulting mixture was stirred at room temperature for 1 h. (S)-5-methoxy-N-propyl-1,2,3,4-tetrahydronaphthalen-2-amine (0.28 g, 1.29 mmol) in DMF (5 mL) was added next to the reaction mixture and stirred at room temperature for an additional 3 h after which DMF was evaporated under vacuum. Water was added and extracted with CH$_2$Cl$_2$ (3×25 mL). The combined organic layer was dried using Na$_2$SO$_4$, and the solvent was removed under reduced pressure. The crude product was purified by silica gel column chromatography (hexane:EtOAc=2:3) to yield compound 10 (0.325 g, 64%). $^1$H NMR (600 MHz, CDCl$_3$): δ 7.24-7.15 (m, 4H), 7.08 (q, J=7.8 Hz, 1H), 6.66-6.60 (m, 2H), 4.58-4.55 (m, 1H), 4.04-3.99 (m, 1H), 3.80 (s, 3H), 3.75 (s, 1H), 3.72 (s, 1H), 3.24-3.12 (m, 2H), 3.02-2.82 (m, 3H), 2.63-2.57 (m, 1H), 2.40-2.34 (m, 1H), 1.97-1.94 (m, 1H), 1.74-1.59 (m, 3H), 0.91-0.87 (m, 3H).

2-(4-{[(6,7-Dimethoxy-1,2,3,4-tetrahydro-naphthalen-2-yl)-propyl-carbamoyl]-methyl}-phenyl)-N-(5-methoxy-1,2,3,4-tetrahydro-naphthalen-2-yl)-N-propyl-acetamide (11)

Compound 10 (0.28 g, 0.71 mmol), 9 (0.177 g, 0.71 mmol), EDC (0.136 g, 0.71 mmol), HOBt (0.096 g, 0.71 mmol) and Et$_3$N (0.1 mL, 0.71 mmol) were reacted in DMF (15 mL) overnight according to procedure A. The crude product was purified by silica gel column chromatography (hexane:EtOAc=2:3) to afford compound 11 (0.325 g, 73%). $^1$H NMR (600 MHz, CDCl$_3$): δ 7.26-7.17 (m, 4H), 7.11-7.06 (m, 1H), 6.67-6.61 (m, 2H), 6.56-6.50 (m, 2H), 4.63-4.57 (m, 1H), 4.06-3.99 (m, 1H), 3.83-3.78 (m, 9H), 3.76-3.71 (m, 4H), 3.24-3.11 (m, 4H), 3.03-2.75 (m, 5H), 2.73-2.58 (m, 3H), 2.42-2.31 (m, 1H), 1.97-1.87 (m, 2H), 1.81-1.63 (m, 5H), 0.92-0.87 (m, 6H); $[α]_D^{25}$=+12.4 (c=1.0 in CH$_2$Cl$_2$).

(6,7-Dimethoxy-1,2,3,4-tetrahydro-naphthalen-2-yl)-[2-(4-{2-[(5-methoxy-1,2,3,4-tetrahydro-naphthalen-2-yl)-propyl-amino]-ethyl}-phenyl)-ethyl]-propyl-amine (12)

To a solution of compound 11 (0.31 g, 0.5 mmol) in anhydrous THF (10 mL), BH$_3$.THF complex (4.95 mL, 4.95 mmol, 1.0 M in THF) was added dropwise at room temperature. Reaction temperature was raised to 55° C. and the mixture was stirred for 4 h. After cooling, water (1 mL) and concentrated HCl (2 mL) were added at 0° C. and then THF was evaporated under vacuum. 25% NaOH solution (20 mL) was added to the aqueous phase and extracted with EtOAc (3×25 mL). The combined organic layer was dried using Na$_2$SO$_4$, and the solvent was removed under reduced pressure. The crude product was purified by silica gel column chromatography (hexane:EtOAc=7:3) to furnish compound 12 (0.205 g, 69%). $^1$H NMR (600 MHz, CDCl$_3$): δ 7.18 (s, 4H), 7.11-7.08 (m, 1H), 6.71 (q, J=7.8 Hz, 1H), 6.65 (d, J=8.4 Hz, 1H), 6.60-6.56 (m, 2H), 3.84-3.79 (m, 9H), 3.30-3.19 (m, 3H), 3.18-3.04 (m, 7H), 3.01-2.73 (m, 10H), 2.57-2.38 (m, 3H), 1.91-1.71 (m, 7H), 0.97-0.93 (m, 6H); $^{13}$C NMR (150 MHz, CDCl$_3$): δ 157.09, 147.41, 137.12, 136.05, 129.24, 127.09, 126.66, 126.23, 124.19, 121.50, 112.03, 111.05, 107.27, 64.44, 64.05, 60.37, 58.72, 55.92, 55.25, 30.13, 29.63, 29.53, 29.45, 24.06, 23.51, 21.05, 16.42, 14.23, 11.88; $[\alpha]_D^{25}$=+10.8 (c=1.0 in CH$_2$Cl$_2$).

6-{[2-(4-{2-[(5-Hydroxy-1,2,3,4-tetrahydro-naphthalen-2-yl)-propyl-amino]-ethyl}-phenyl)-ethyl]-propyl-amino}-5,6,7,8-tetrahydro-naphthalene-2,3-diol (13) (D-679)

A mixture of compound 12 (0.2 g, 0.33 mmol) and 48% aqueous HBr (15 mL) was refluxed at 130° C. for 5 h. The reaction mixture was evaporated to dryness, washed with ether followed by vacuum drying to yield HBr salt of 13 (0.22 g, 89%). $^1$H NMR (600 MHz, CD$_3$OD): δ 7.31 (t, J=7.8 Hz, 4H), 6.85 (t, J=7.2 Hz, 1H), 6.63 (d, J=7.8 Hz, 1H), 6.57-6.52 (m, 2H), 6.47 (s, 1H), 3.64-3.62 (m, 2H), 3.46-3.32 (m, 4H), 3.27-3.13 (m, 9H), 3.01-2.88 (m, 4H), 2.68 (bs, 1H), 2.54-2.46 (m, 1H), 2.32-2.26 (m, 2H), 1.84-1.76 (m, 6H), 1.02 (t, J=7.2 Hz, 6H); $^{13}$C NMR (150 MHz, CD$_3$OD): δ 154.53, 143.73, 143.41, 135.52, 133.56, 129.27, 126.61, 125.78, 122.99, 121.73, 120.09, 115.39, 114.66, 112.24, 60.88, 60.52, 52.57, 52.31, 52.14, 51.82, 30.46, 29.47, 28.66, 27.31, 24.11, 23.48, 22.36, 18.54, 10.31; $[\alpha]_D^{25}$=+7.8 (c=0.5 in CH$_3$OH); Anal. Calcd for C$_{36}$H$_{53}$Br$_2$N$_2$O$_{4.5}$: C, 57.99; H, 7.16; N, 3.76. Found: C, 57.94; H, 7.03; N, 3.81.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having formula I for treating a neurodegenerative disease:

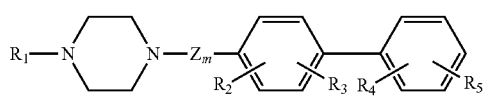

I or a pharmaceutically acceptable salt or ester or carbamate thereof,
wherein:
$R_1$ is H, $C_{1-8}$ alkyl, $C_{2-8}$ alkenyl, $C_{4-8}$ cycloalkyl, $C_{4-8}$ cycloalkenyl, $C_{6-10}$ aryl, $C_{1-10}$ alkyl $C_{6-10}$ aryl, or

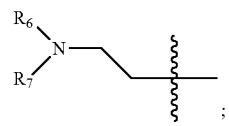

$R_2$, $R_3$, $R_4$, $R_5$ are each independently H or OH wherein at least 2 of $R_2$, $R_3$, $R_4$, $R_5$ are OH;
$R_6$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, an optionally substituted $C_{1-8}$ alkyl $C_{6-10}$ aryl, or an optionally substituted $C_{6-10}$ aryl;
$R_7$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, an optionally substituted $C_{1-8}$ alkyl $C_{6-10}$ aryl, or an optionally substituted $C_{6-10}$ aryl;
$Z_m$ is absent or a divalent linking moiety in which Z is repeated m times; and
m is 0, 1, 2, 3, 4, or 5.

2. The compound of claim 1 wherein $R_1$ is

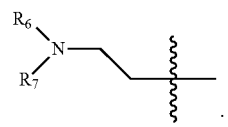

3. The compound of claim 1 wherein $R_6$ and $R_7$ are each independently $C_{1-8}$ alkyl, $C_{2-8}$ alkenyl, $C_{2-8}$ alkynyl, $C_{4-8}$ cycloalkyl, or $C_{4-8}$ cycloalkenyl, an optionally substituted $C_{1-8}$ alkyl $C_{6-10}$ aryl.

4. The compound of claim 1 having a formula selected from the group consisting of:

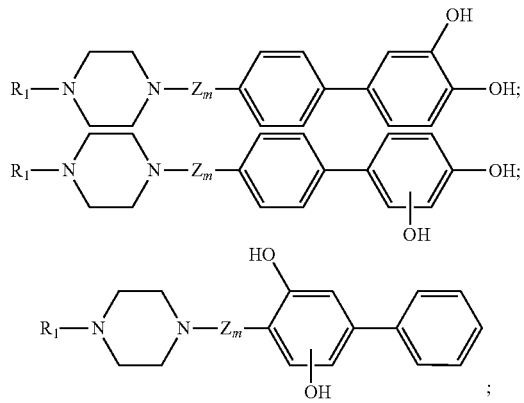

pharmaceutically acceptable salts thereof; esters thereof; and carbamates thereof.

5. The compound of claim 1 having a formula selected from the group consisting of:

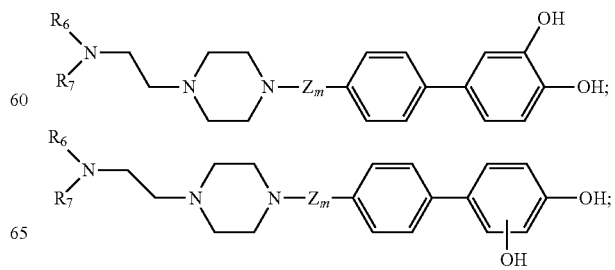

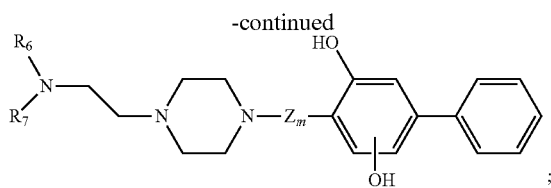

pharmaceutically acceptable salts thereof;
esters thereof; and
carbamates thereof.

6. The compound of claim 1 having the following formula:

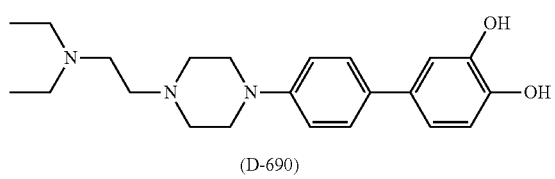

(D-690)

or a pharmaceutically acceptable salt or ester or carbamate thereof.

7. The compound of claim 1 having the following formula:

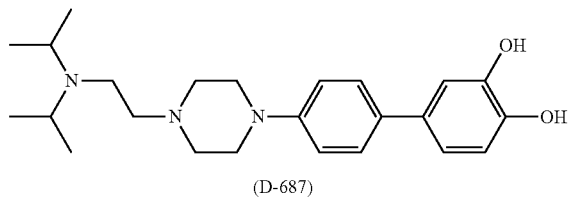

(D-687)

or a pharmaceutically acceptable salt or ester or carbamate thereof.

8. The compound of claim 1 having the following formula:

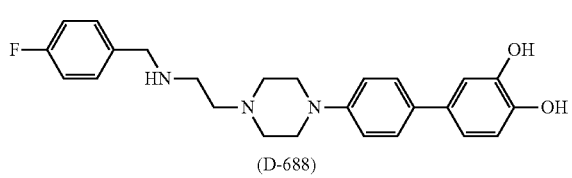

(D-688)

or a pharmaceutically acceptable salt or ester or carbamate thereof.

9. The compound of claim 1 wherein $R_7$ is substituted with a component selected from the group consisting of, halogen, $C_{1-8}$ alkyl, $C_{1-8}$ alkoxy, $C_{1-4}$ acyloxy, $C_{1-4}$ acyl, —C(O)—$R_9$, —$R_{10}$—NH—$SO_2$—N($R_9$)$_r$, —$R_{10}$—NH—C(O)—$R_9$; —$R_{10}$—N($R_9$)r, and —$R_9$—Ar where
$R_9$ is H, $C_{1-8}$ alkyl, $C_{2-8}$ alkenyl, $C_{4-8}$ cycloalkyl, $C_{4-8}$ cycloalkenyl, or $C_{6-10}$ aryl;
$R_{10}$ is $C_{2-8}$ alkenyl;
r is 2 or 3; and
Ar is bipyridyl, biphenylyl, or a $C_{6-10}$ aryl ring system, optionally including one or more heteroatoms or $C_{5-10}$ heteroaryl; with the proviso that when r is 3, the nitrogen of the N($R_9$)$_r$ group will bear a positive formal charge.

10. The compound of claim 9 wherein Ar is an optionally substituted phenyl, thienyl, pyridyl, bipyridyl, biphenylyl, or naphthyl.

11. The compound of claim 1 wherein Z is selected from the group consisting of —$CH_2$—, —CHOH$CH_2$—, —CHOH$CH_2CH_2$—, —CHOH$CH_2CH_2CH_2$—, —CO—, —N—$CH_2$—, —N—CO—, —($CH_2$)$_n$—, —CHOH($CH_2$)$_n$—, —($CH_2$)$_n$CO—, —($CH_2$)$_n$NCO($CH_2$)$_k$—, $C_{1-10}$ carboximido, $C_{2-10}$ alkanediyl, $C_{2-10}$ alkynediyl, and combinations thereof; m is 1, 2, 3, 4, or 5, and n and k are each independently integers 1, 2, 3, 4, 5, 6, 7, or 8.

12. The compound of claim 1 wherein:
$R_6$ is $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{1-8}$ alkyl $C_{6-10}$ aryl, or $C_{6-10}$ aryl; and
$R_7$ is $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{1-8}$ alkyl $C_{6-10}$ aryl, or $C_{6-10}$ aryl.

13. The compound of claim 1 wherein:
$R_6$ is $C_{1-8}$ alkyl, $C_{4-8}$ cycloalkyl, $C_{1-8}$ alkyl $C_{6-10}$ aryl, or $C_{6-10}$ aryl; and
$R_7$ is $C_{1-8}$ alkyl, $C_{4-8}$ cycloalkyl, $C_{1-8}$ alkyl $C_{6-10}$ aryl, or $C_{6-10}$ aryl.

14. The compound of claim 1 wherein:
$R_6$ is $C_{1-8}$ alkyl, $C_{4-8}$ cycloalkyl, or $C_{1-8}$ alkyl $C_{6-10}$ aryl; and
$R_7$ is $C_{1-8}$ alkyl or $C_{4-8}$ cycloalkyl.

15. The compound of claim 1 wherein Z is absent and m is 0.

16. A compound for treating a neurodegenerative disease, the compound having formula 1, 2, 3, or 4:

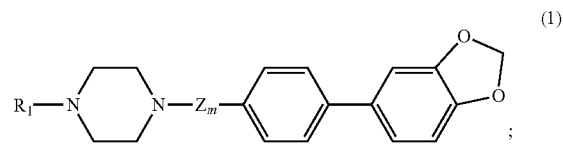

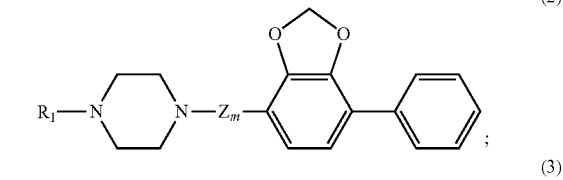

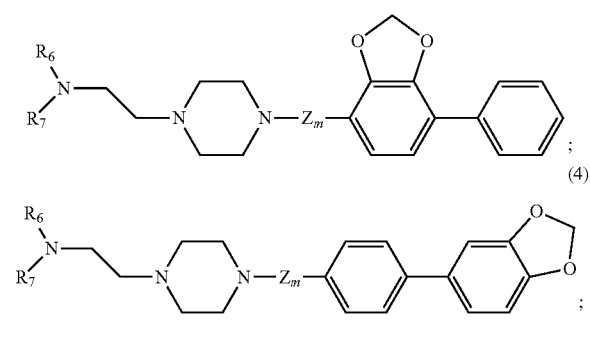

or a pharmaceutically acceptable salts thereof or an ester thereof; or a carbamate thereof,
wherein:
$R_1$ is H, methyl, $C_{2-8}$ alkenyl, $C_{4-8}$ cycloalkyl, $C_{4-8}$ cycloalkenyl, $C_{6-10}$ aryl, $C_{1-10}$ alkyl $C_{6-10}$ aryl, or

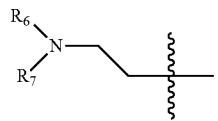

$R_6$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, an optionally substituted $C_{1-8}$ alkyl $C_{6-10}$ aryl, or an optionally substituted $C_{6-10}$ aryl;

$R_7$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, an optionally substituted $C_{1-8}$ alkyl $C_{6-10}$ aryl, or an optionally substituted $C_{6-10}$ aryl;

$Z_m$ is absent or a divalent linking moiety in which Z is repeated m times;

Z is —$CH_2$—, —$CHOHCH_2$—, —$CHOHCH_2CH_2$—, —$CHOHCH_2CH_2CH_2$—, —$CO$—, —$N$—$CH_2$—, —$N$—$CO$—, —$CHOH(CH_2)_n$—, —$(CH_2)_nCO$—, or —$(CH_2)_nNCO(CH_2)_k$;

n and k are each independently integers 1, 2, 3, 4, 5, 6, 7, or 8; and
m is 0, 1, or 2.

17. The compound of claim 16 wherein $R_7$ is substituted with a component selected from the group consisting of, halogen, $C_{1-8}$ alkyl, $C_{1-8}$ alkoxy, $C_{1-4}$ acyloxy, $C_{1-4}$ acyl, —C(O)—$R_9$, —$R_{10}$—NH—$SO_2$—$N(R_9)_r$, —$R_{10}$—NH—C(O)—$R_9$; —$R_{10}$—$N(R_9)$r, and —$R_9$—Ar where
$R_9$ is H, $C_{1-8}$ alkyl, $C_{2-8}$ alkenyl, $C_{4-8}$ cycloalkyl, $C_{4-8}$ cycloalkenyl, or $C_{6-10}$ aryl;
$R_{10}$ is $C_{2-8}$ alkenyl;
r is 2 or 3; and
Ar is bipyridyl, biphenylyl, or a $C_{6-10}$ aryl ring system, optionally including one or more heteroatoms or $C_{5-10}$ heteroaryl; with the proviso that when r is 3, the nitrogen of the $N(R_9)_r$ group will bear a positive formal charge.

18. The compound of claim 17 wherein Ar is an optionally substituted phenyl, thienyl, pyridyl, bipyridyl, biphenylyl, or naphthyl.

19. The compound of claim 16 wherein:
$R_6$ is $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{1-8}$ alkyl $C_{6-10}$ aryl, or $C_{6-10}$ aryl; and
$R_7$ is $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{1-8}$ alkyl $C_{6-10}$ aryl, or $C_{6-10}$ aryl.

20. The compound of claim 16 wherein:
$R_6$ is $C_{1-8}$ alkyl, $C_{4-8}$ cycloalkyl, $C_{1-8}$ alkyl $C_{6-10}$ aryl, or $C_{6-10}$ aryl; and
$R_7$ is $C_{1-8}$ alkyl, $C_{4-8}$ cycloalkyl, $C_{1-8}$ alkyl $C_{6-10}$ aryl, or $C_{6-10}$ aryl.

21. The compound of claim 16 wherein:
$R_6$ is $C_{1-8}$ alkyl, $C_{4-8}$ cycloalkyl, or $C_{1-8}$ alkyl $C_{6-10}$ aryl; and
$R_7$ is $C_{1-8}$ alkyl or $C_{4-8}$ cycloalkyl.

22. The compound of claim 16 wherein Z is absent and m is 0.

23. A compound selected from the group consisting of:

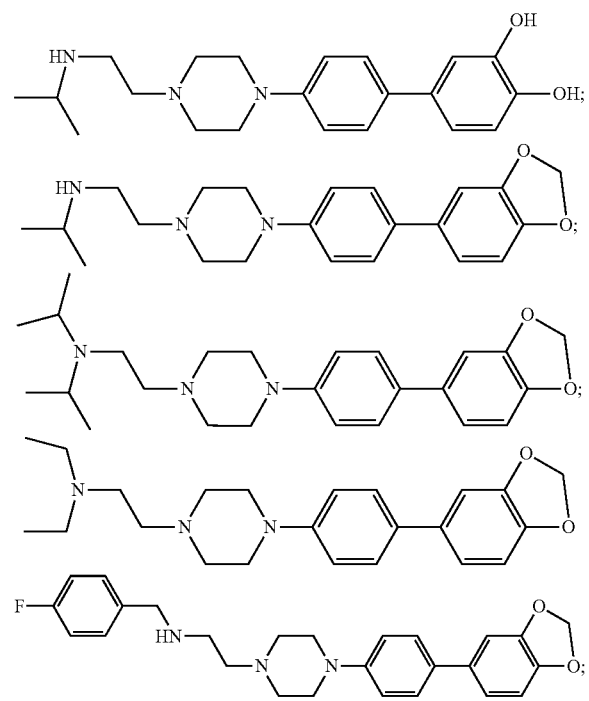

pharmaceutically acceptable salts thereof esters thereof; and carbamates thereof.

24. The compound of claim 16 wherein $Z_m$ is a divalent linking moiety in which Z is repeated m times and m is 1.

25. A compound for treating a neurodegenerative disease, the compound having formula 1, 2, 3, or 4:

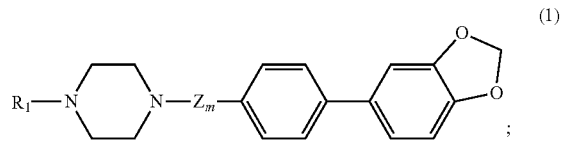

(1)

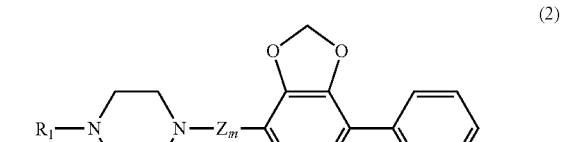

(2)

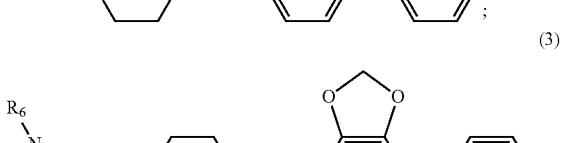

(3)

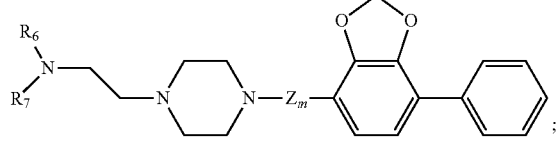

-continued

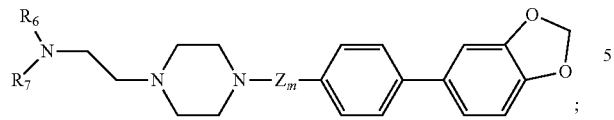
(4)

or a pharmaceutically acceptable salts thereof or an ester thereof; or a carbamate thereof,
wherein:
$R_1$ is H, $C_{1-8}$ alkyl, $C_{2-8}$ alkenyl, $C_{4-8}$ cycloalkyl, $C_{4-8}$ cycloalkenyl, $C_{6-10}$ aryl, $C_{1-10}$ alkyl $C_{6-10}$ aryl, or

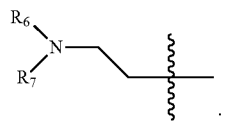

$R_6$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, an optionally substituted $C_{1-8}$ alkyl $C_{6-10}$ aryl, or an optionally substituted $C_{6-10}$ aryl;

$R_7$ is H, an optionally substituted $C_{1-8}$ alkyl, an optionally substituted $C_{1-8}$ alkoxyl, an optionally substituted $C_{2-8}$ alkenyl, an optionally substituted $C_{2-8}$ alkynyl, an optionally substituted $C_{4-8}$ cycloalkyl, an optionally substituted $C_{4-8}$ cycloalkenyl, an optionally substituted $C_{1-8}$ alkyl $C_{6-10}$ aryl, or an optionally substituted $C_{6-10}$ aryl;

$Z_m$ is absent or a divalent linking moiety in which Z is repeated m times;

Z is —$CH_2$—, —$CHOHCH_2$—, —$CHOHCH_2CH_2$—, —$CHOHCH_2CH_2CH_2$—, —N—$CH_2$—, —N—CO—, —$CHOH(CH_2)_n$—, —$(CH_2)_nCO$—, or —$(CH_2)_nNCO(CH_2)_k$;

n and k are each independently integers 1, 2, 3, 4, 5, 6, 7, or 8; and m is 0, 1, or 2.

* * * * *